United States Patent [19]

Miyake et al.

[11] Patent Number: 5,491,145
[45] Date of Patent: Feb. 13, 1996

[54] IMIDAZOPYRIDAZINES, THEIR PRODUCTION AND USE

[75] Inventors: Akio Miyake, Hirakata; Yasuhiko Kawano, Suita; Yasuko Ashida, Takatsuki, all of Japan

[73] Assignee: Takeda Chemical Industries, Ltd., Osaka, Japan

[21] Appl. No.: 345,326

[22] Filed: Nov. 21, 1994

Related U.S. Application Data

[63] Continuation of Ser. No. 32,297, Mar. 17, 1993, abandoned.

[30] Foreign Application Priority Data

Mar. 18, 1992 [JP] Japan ..................... 4-061883
Jan. 26, 1993 [JP] Japan ..................... 5-010917

[51] Int. Cl.$^6$ ..................... A61K 31/50; C07D 487/04
[52] U.S. Cl. ..................... 514/248; 544/117; 544/232; 544/234; 544/236; 544/383; 558/12; 560/125; 560/150; 560/226; 560/266; 564/95; 568/613; 568/681
[58] Field of Search ..................... 514/248; 544/232, 544/236, 117

[56] References Cited

U.S. PATENT DOCUMENTS

| | | | |
|---|---|---|---|
| 5,145,850 | 9/1992 | Miyake et al. | 544/236 |
| 5,155,108 | 10/1992 | Miyake et al. | 544/236 |
| 5,202,324 | 4/1993 | Miyake et al. | 544/236 |

FOREIGN PATENT DOCUMENTS

| | | |
|---|---|---|
| 0381132 | 8/1990 | European Pat. Off. . |
| 0440119 | 8/1991 | European Pat. Off. . |
| 0444549 | 9/1991 | European Pat. Off. . |

*Primary Examiner*—Emily Bernhardt
*Attorney, Agent, or Firm*—Foley & Lardner

[57] ABSTRACT

Novel compound of the general formula:

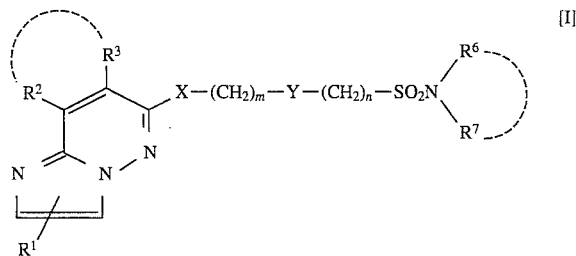

wherein $R^1$ stands for a hydrogen atom, an optionally substituted lower alkyl group or a halogen atom; $R^2$ and $R^3$ respectively stand for a hydrogen atom or an optionally substituted lower alkyl group, provided that either $R^2$ or $R^3$ is a hydrogen atom, the other being an optionally substituted lower alkyl group, or $R^2$ and $R^3$ may, taken together with the adjacent —C=C— group, form a 5- to 7-membered ring; X stands for an oxygen atom or $S(O)_p$ (p stands for an integer from 0 to 2; Y stands for a group of the formula:

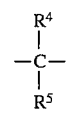

($R^4$ and $R^5$ respectively stand for a hydrogen atom or an optionally substituted lower alkyl group) or a divalent group derived from an optionally substituted 3- to 7-membered homocyclic or heterocyclic ring; $R^6$ and $R^7$ each stands for a hydrogen atom, an optionally substituted lower lakyl group, an optionally substituted cycloalkyl group or an optionally substituted aryl group, or $R^6$ and $R^7$ may, taken together with the adjacent nitrogen atom, form an optionally substituted nitrogen-containing heterocyclic group; m stands for an integer from 0 to 4; and n stands for an integer from 0 to 4, or a salt thereof, which has excellent anti-PAF activities, and is of value as an antiasthmatic agent, and their production, intermediates and pharmaceutical compositions.

17 Claims, No Drawings

IMIDAZOPYRIDAZINES, THEIR PRODUCTION AND USE

This application is a continuation of application Ser. No. 08/032,297, filed Mar. 17, 1993, now abandoned.

FIELD OF THE INVENTION

The present invention relates to a new substituted imidazopyridazine derivative or a salt thereof, a method of production thereof, an intermediate and a composition. Possessing antiallergic, anti-inflammatory and anti-PAF (platelet activating factor) activities, the imidazopyridazine derivative or a salt thereof of the present invention serves well as an antiasthmatic drug by suppressing bronchospasm and bronchoconstriction.

BACKGROUND OF THE INVENTION

At present, attempts are being made to synthesize a large number of new imidazopyridazine compounds serving as effective drugs against a variety of diseases. For example, EP-0,381,130 describes a compound represented by the formula:

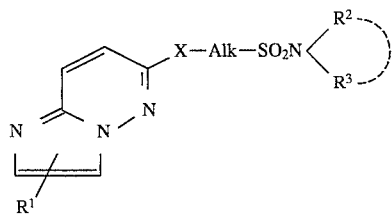

wherein $R^1$ represents a hydrogen atom, a lower alkyl group which may be substituted, or a halogen atom; $R^2$ and $R^3$ independently represent a hydrogen atom, a lower alkyl group which may be substituted, a cycloalkyl group which may be substituted, or a phenyl group which may be substituted; $R^2$ and $R^3$ may cooperate with the adjacent nitrogen atom to form a heterocyclic ring which may be substituted; X represents an oxygen atom or $S(O)_n$ (n is an integer from 0 to 2); Alk represents a linear or branched $C_{1-10}$ alkylene, provided that X is an oxygen atom, when (i) $R^1$ is a hydrogen atom, and (ii) either $R^2$ or $R^3$ is a hydrogen atom, the other being a hydrogen atom or a lower alkyl, and (iii) Alk is a linear $C_{2-4}$ alkylene, or a salt thereof. EP-0,440,119 describes a compound represented by the formula:

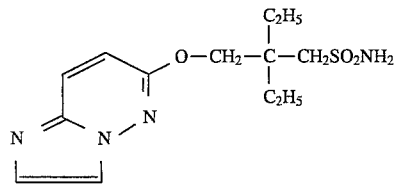

or a salt thereof.

EP-0,444,549 describes a compound represented by the formula:

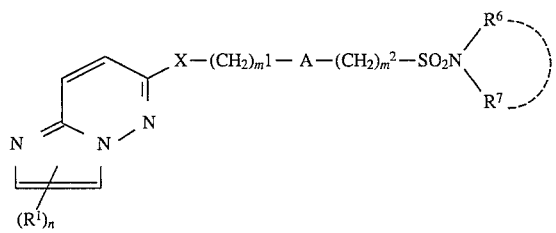

wherein $R^1$ represents a halogen atom or a lower alkyl group which may be substituted; $R^2$ and $R^3$ independently represent a hydrogen atom, a lower alkyl group which may be substituted, a cycloalkyl group which may be substituted, or a phenyl group which may be substituted; $R^2$ and $R^3$ may cooperate with the adjacent nitrogen atom to form a heterocyclic ring which may be substituted; X represents an oxygen atom or $S(O)_k$ (k is an integer from 0 to 2); the —A— group is a divalent 3- to 7-membered homocyclic or heterocyclic ring; $m^1$ and $m^2$ independently represent an integer from 0 to 4 and n represents an integer from 0 or 1, or a salt thereof. These compounds are shown to possess antiasthmatic activity.

OBJECT OF THE INVENTION

Although a wide variety of antiasthmatic drugs are now commercially available, none are satisfactory as to action sustainability, safety and other properties. It is therefore desired that a new compound be developed which exhibits more antiallergic, anti-inflammatory and anti-PAF activities and which is excellent in action sustainability, safety and other properties for an antiasthmatic drug.

SUMMARY OF THE INVENTION

The present inventors investigated the chemical modification of imidazo[1,2-b]pyridazine compounds at the 7- and 8-positions, and found that a new imidazo[1,2-b]pyridazine compounds structurally different from the above known compounds unexpectedly exhibit highly antiallergic, anti-inflammatory and anti-PAF activities and excellent action sustainability and safety. The inventors also found that these compounds can serve as effective antiasthmatic drugs, since they suppress bronchospasm and bronchoconstriction. The inventors made further investigations based on these findings, and completed the present invention.

Accordingly, the present invention provides:

(1) a compound (or a salt thereof) represented by the formula:

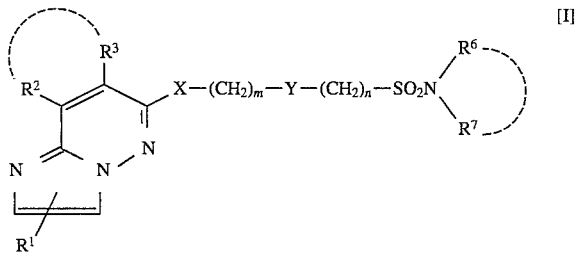

wherein $R^1$ represents a hydrogen atom, a lower alkyl group which may be substituted, or a halogen atom; $R^2$ and $R^3$ independently represent a hydrogen atom or a lower alkyl group which may be substituted, provided that either $R^2$ or $R^3$ is a hydrogen atom, the other being a lower alkyl group which may be substituted; $R^2$ and $R^3$ may cooperate with the adjacent —C=C— to form a 5- to 7-membered ring; X represents an oxygen atom or S(O)$_p$ (p represents an integer from 0 to 2); Y represents a group represented by the formula:

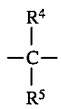

wherein R$^4$ and R$^5$ independently represent a hydrogen atom or a lower alkyl group which may be substituted, or a divalent group derived from a 3- to 7-membered homocyclic or heterocyclic ring which may be substituted; R$^6$ and R$^7$ independently represent a hydrogen atom, a lower alkyl group which may be substituted, a cycloalkyl group which may be substituted, or an aryl group which may be substituted; R$^6$ and R$^7$ may cooperate with the adjacent nitrogen atom to form a nitrogen-containing heterocyclic ring which may be substituted; m represents an integer from 0 to 4 and n represents an integer from 0 to 4, or a salt thereof, (2) a method of producing the compound of the item (1) by carrying out a reaction between a compound represented by the formula:

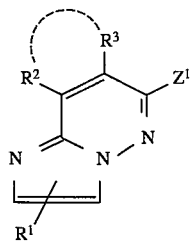
[II]

wherein Z$^1$ represents a reactive group; and R$^1$, R$^2$ and R$^3$ are as described above, or a salt thereof, and a compound represented by the formula:

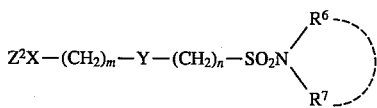
[III]

wherein Z$^2$ represents a group which splits off upon reaction with Z$^1$; and X, Y, R$^6$, R$^7$, m and n are as described above, or a alt thereof, (3) a method of producing the compound of the item (1) by carrying out a reaction between a compound represented by the formula:

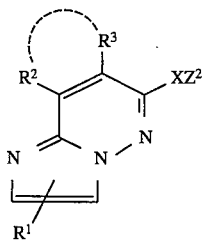
[IV]

wherein Z$^2$, R$^1$, R$^2$, R$^3$ and X are as described above, or a salt thereof and a compound represented by the formula:

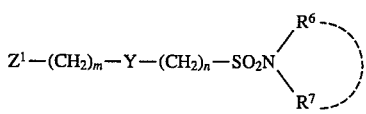
[V]

wherein Z$^1$, Y, R$^6$, R$^7$, m and n are as described above, or a salt thereof, (4) a method of producing the compound of the item (1) by carrying out a reaction between a compound represented by the formula:

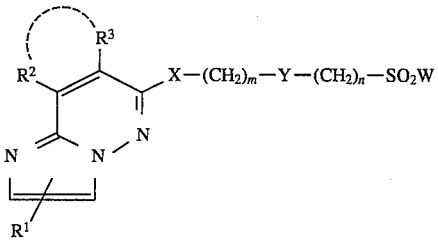
[VI]

wherein W represents a splitting group; and R$^1$, R$^2$, R$^3$, X, Y, m and n are as described above, or a salt thereof, and a compound represented by the formula:

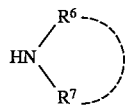
[VII]

wherein R$^6$ and R$^7$ are as described above, or a salt thereof, (5) an antiasthmatic drug containing a compound [I] or a salt thereof, and (6) a compound [VI] or a salt thereof.

Provided that a compound [I] or a salt thereof contains an asymmetric carbon in its molecular structure, optical isomers and racemic mixtures are included in the scope of the present invention.

The term "lower alkyl" as used herein means a straight or branched C$_{1-6}$ alkyl group, for instance. Usable C$_{1-6}$ alkyl groups include methyl, ethyl, n-propyl, isopropyl, n-butyl, isobutyl, tert-butyl, n-pentyl, n-hexyl and so on.

The term "cycloalkyl group" means a C$_{3-6}$ cycloalkyl group, for instance. Usable C$_{3-6}$ cycloalkyl groups include cyclopropyl, cyclobutyl, cyclopentyl, cyclohexyl and so on.

The term "aryl group" means a C$_{6-14}$ aryl group, for instance. Usable C$_{6-14}$ aryl groups include phenyl, naphthyl and so on.

Examples of substituents for said "lower alkyl" and "cycloalkyl group" include hydroxy, amino, carboxyl, nitro, mono- or di-lower alkylamino (e.g., mono- or di-C$_{1-6}$ alkylamino such as methylamino, ethylamino, propylamino, dimethylamino and diethylamino), lower alkoxy (e.g., C$_{1-6}$ alkoxy such as methoxy, ethoxy, propoxy and hexyloxy), lower alkyl-carbonyloxy (e.g., C$_{1-6}$ alkyl-carbonyloxy such as acetoxy and ethylcarbonyloxy), halogen atom (e.g., fluorine, chlorine, bromine, iodine and so on) and so on, of which substituents an number of one to four is selected.

Example substituents for said "aryl group" include lower alkyl which may be substituted, amino which may be substituted, hydroxy, carboxyl, nitro, lower alkoxy (e.g., C$_{1-6}$ alkoxy such as methoxy, ethoxy and propoxy), lower alkyl-carbonyloxy (e.g., C$_{1-6}$ alkyl-carbonyloxy such as acetoxy and ethylcarbonyloxy), halogen atom (e.g., fluorine, chlorine, bromine, iodine and so on) and so on, of which substituents an number of one to five is selected. Example substituents for said lower alkyl include hydroxy, amino, mono- or di-lower alkylamino (e.g., mono- or di-C$_{1-6}$ alkylamino such as methylamino, ethylamino, propylamino, dimethylamino and diethylamino), lower alkoxy (e.g., C$_{1-6}$ alkoxy such as methoxy, ethoxy, propoxy and hexyloxy), halogen atom (e.g., fluorine, chlorine, bromine, iodine and so on) and so on, of which substituents an number of one to four is selected. Example substituents for said amino group include C$_{1-6}$ alkyl (e.g., methyl, ethyl, propyl and so on), acyl (e.g., C$_{1-6}$ acyl such as formyl, acetyl, propionyl and butyryl) and 5- to 7-membered cyclic amino (e.g., pyrrolidino, morpholino, piperidino, piperazino and so on), of which substituents 1 or 2 are selected.

Substituents under the definition of the term "halogen atom" include fluorine, chlorine, bromine and iodine and so on.

The term "5- to 7-membered ring formed in cooperation with the adjacent —C=C—" means a 5- to 7-membered ring which may have one to four hetero atoms, for example, selected from nitrogen, oxygen, sulfur and other atoms in addition to carbon atoms. Specifically, for example, $C_{5-7}$ cycloalkene such as cyclopentene, cyclohexene and cycloheptene, 5- to 7-membered hydrocarbon rings such as benzene, and 5- to 7-membered nitrogen-containing heterocyclic group comprising carbon atoms and nitrogen atoms, such as pyrrole, pyridine and piperidine, are often used.

The term "3- to 7-membered homocyclic ring" means a 3- to 7-membered homocyclic ring comprising carbon atoms only, for instance. Specifically, $C_{3-7}$ cycloalkane such as cyclopropane, cyclobutane, cyclopentane, cyclohexane and cycloheptane, $C_{3-7}$ cycloalkene such as cyclopropene, cyclobutene, cyclopentene, cyclohexene and cycloheptene, and benzene, for instance, are often used.

The divalent group derived from said "3- to 7-membered homocyclic ring" is a group resulting from either elimination of two hydrogen atoms from a single carbon atom in the 3- to 7-membered homocyclic ring or elimination of one hydrogen atom from each of two different carbon atoms such as $C_{3-7}$ cycloalkylene and naphthalene. Specifically, the following groups, for instance, are used.

Of these, the following groups, for instance, are often used.

More preferable examples in above groups include the following groups:

The term "3- to 7-membered heterocyclic ring" means a 3- to 7-membered heterocyclic ring which may have one to four hetero atoms, for example, selected from nitrogen, oxygen, sulfur and other atoms in addition to carbon atoms. Specifically, oxyethane, tetrahydrofuran, tetrahydropyran, pyrrole, azetidine, pyrrolidine, piperidine, piperazine, tetrahydrothiophene, homopiperidine, morpholine and so on, for instance, are used.

The divalent group derived from said "3- to 7-membered heterocyclic ring" is a group resulting from either elimination of two hydrogen atoms from a single carbon atom or elimination of one hydrogen atom from each of two different carbon atoms in the 3- to 7-membered heterocyclic ring. Specifically, the following groups, for instance, are used.

The term "nitrogen-containing heterocyclic group" means a group resulting from elimination of one hydrogen atom from a nitrogen atom in a ring such as a 3- to 13-membered nitrogen-containing heterocyclic ring which contains one nitrogen atom in addition to carbon atoms and which may also contain one to four hetero atoms, for example, selected from nitrogen, oxygen, sulfur and other atoms. Specifically, the following, for instance, are used.

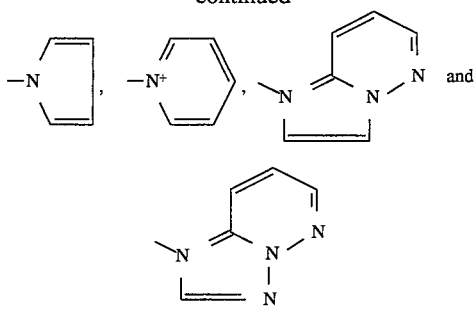

Of these, the following 3- to 9-membered nitrogen-containing heterocyclic groups, for instance, are often used.

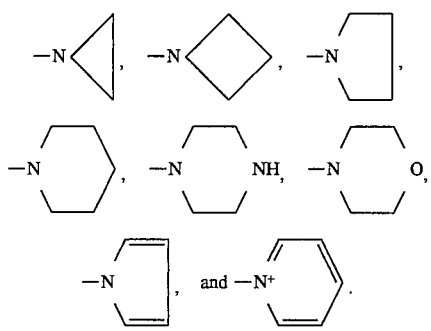

Example substituents for said "3- to 7-membered homocyclic ring," "3- to 7-membered heterocyclic ring" and "nitrogen-containing heterocyclic group" include a lower alkyl which may be substituted, an amino which may be substituted, hydroxy, carboxyl, nitro, lower alkoxy (e.g., $C_{1-6}$ alkoxy such as methoxy, ethoxy and propoxy), halogen atom (e.g., fluorine, chlorine, bromine iodine and so on) and so on, of which substituents an number of one to five is selected. Example substituents for said lower alkyl include a hydroxy, amino, mono- or di-lower alkylamino (e.g., mono- or di-$C_{1-6}$ alkylamino such as methylamino, ethylamino, propylamino, dimethylamino and diethylamino), lower alkoxy (e.g., $C_{1-6}$ alkoxy such as methoxy, ethoxy, propoxy and hexyloxy), lower alkyl-carbonyloxy (e.g., $C_{1-6}$ alkyl-carbonyloxy such as acetoxy and ethylcarbonyloxy), halogen atom (e.g., fluorine, chlorine, bromine, iodine and so on) and so on, of which substituents a number of one to four is selected. Example substituents for said amino group include a $C_{1-6}$ alkyl (e.g., methyl, ethyl, propyl and so on), acyl (e.g., $C_{1-6}$ acyls such as formyl, acetyl, propionyl and butyryl), 5- to 7-membered cyclic amino (e.g., pyrrolidino, morpholino, piperidino, piperazino and so on), of which substituents one or two is selected.

With respect to the above formula, $R^1$ represents a hydrogen atom, a lower alkyl group which may be substituted, or a halogen atom. $R^1$ is preferably a hydrogen atom or a $C_{1-3}$ alkyl (e.g., methyl, ethyl, n-propyl), for instance, with a hydrogen atom often used.

$R^2$ and $R^3$ independently represent a hydrogen atom or a lower alkyl group which may be substituted, and $R^2$ and $R^3$ may cooperate with the adjacent —C=C— to form a 5- to 7-membered ring. Provided that either $R^2$ or $R^3$ is a hydrogen atom, the other being a lower alkyl group which may be substituted.

For $R^2$ and $R^3$, hydrogen atom and $C_{1-3}$ alkyl (e.g., methyl, ethyl, n-propyl and so on), for instance, are preferable, with hydrogen atom or methyl often used. More preferably, $R^2$ is a hydrogen atom and $R^3$ is a $C_{1-3}$ alkyl group. It is also preferable that $R^2$ and $R^3$ cooperate with the adjacent —C=C— to form a 5- to 7-membered homocyclic ring, specifically cyclohexene or benzene, for instance.

X represents an oxygen atom or $S(O)_p$ (p represents an integer from 0 to 2). X is preferably an oxygen atom or S, for instance, with an oxygen atom often used.

Y represents a group represented by the formula:

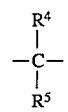

wherein $R^4$ and $R^5$ independently represent a hydrogen atom or a lower alkyl group which may be substituted, or a divalent group derived from a 3- to 7-membered homocyclic or heterocyclic ring which may be substituted. Y is preferably a group represented by the formula:

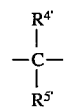

wherein $R^{4'}$ and $R^{5'}$ independently represent a hydrogen atom or a $C_{1-3}$ alkyl which may be substituted, for instance.

Example $C_{1-3}$ alkyl for "$C_{1-3}$ alkyls which may be substituted" represented by $R^{4'}$ and $R^{5'}$ include such as methyl, ethyl, n-propyl and isopropyl. Example substituents are the same as those "lower alkyl" may have. $R^{4'}$ and $R^{5'}$ are often independently a hydrogen atom or a $C_{1-3}$ alkyl (e.g., methyl, ethyl, n-propyl and so on), more preferably $R^{4'}$ and $R^{5'}$ independently represent a $C_{1-3}$ alkyl group.

It is also preferable that Y be a divalent group derived from a 3- to 7-membered homocyclic or heterocyclic ring which may be substituted. Examples of such groups include the following groups:

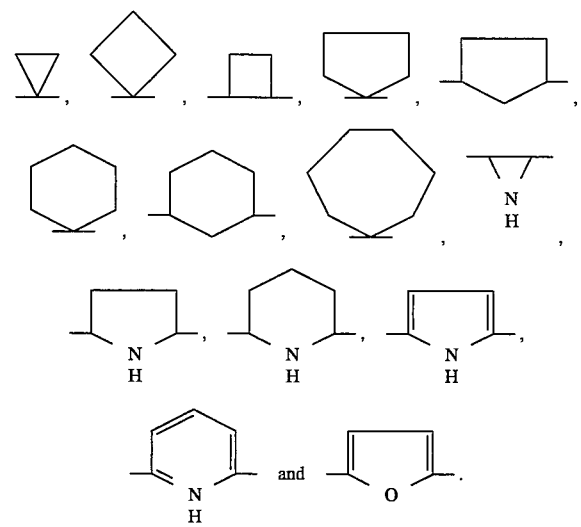

Of these, the following groups, for instance, are often used.

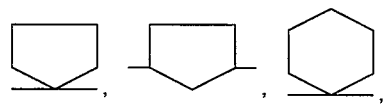

-continued

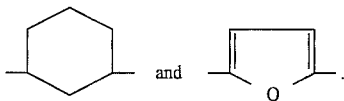

More preferably examples of Y include the follow:

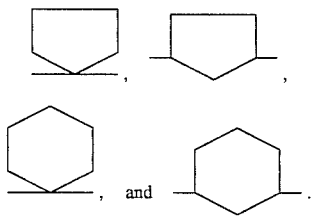

$R^6$ and $R^7$ independently represent a hydrogen atom, a lower alkyl group which may be substituted, a cycloalkyl group which may be substituted, or an aryl group which may be substituted, and $R^6$ and $R^7$ may cooperate with the adjacent nitrogen atom to form a nitrogen-containing heterocyclic group which may be substituted.

For $R^6$ and $R^7$, hydrogen atom and $C_{1-3}$ alkyl (e.g., methyl, ethyl, n-propyl and so on) are preferable, with hydrogen atoms often used. m represents an integer from 0 to 4, preferably 1 to 4, and often 1, for instance. n represents an integer from 0 to 4, preferably 1 to 4, and often 1, for instance. Most preference is given to cases where m is i and n is 1 to 4.

The salt of compound [I] of the present invention is preferably a physiologically acceptable acid adduct salt. Such salts include salts with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid). Provided that compound [I] of the present invention has an acidic group, such as —COOH, it may form a salt with an inorganic base (e.g., an alkali metal or alkaline earth metal such as sodium, potassium, calcium or magnesium; or ammonia) or an organic base (e.g., a tri-$C_{1-3}$ alkylamine such as triethylamine).

A method of producing the compound [I] of the present invention or a salt thereof is described below.

Compound [I] of the present invention or a salt thereof can be prepared by carrying out a reaction (A) between a compound represented by the formula:

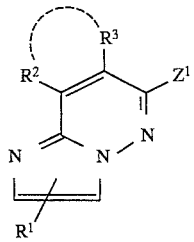 [II]

wherein $Z^1$, $R^1$, $R^2$ and $R^3$ are as described above, or a salt thereof and a compound represented by the formula:

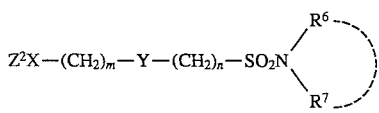 [III]

wherein $Z^2$, X, Y, $R^6$, $R^7$, m and n are as described above, or a salt thereof.

The reactive group represented by $Z^1$ is exemplified by halogen (e.g., chlorine, bromide, iodine), $C_{6-10}$ arylsulfonyloxy (e.g., benzenesulfonyloxy, p-tolylsulfonyloxy) and $C_{1-4}$ alkylsulfonyloxy (e.g., methanesulfonyloxy).

The group which splits off upon reaction with $Z^1$, represented by $Z^2$, is hydrogen or an alkali metal such as sodium or potassium, for instance, provided that X is an oxygen atom or a sulfur atom. Provided that X is —SO— or —SO$_2$—, an alkali metal such as sodium or potassium, for instance, is used.

In this reaction, compound [IN] or a salt thereof is used at normally 1 to 5 mol, preferably 1 to 2 mol per mol of compound [II] or a salt thereof.

In this reaction, it is recommended that condensation be carried out in the presence of a base. Example bases include alkali metal hydrides such as sodium hydride and potassium hydride, alkali metal alkoxides such as sodium methoxide and sodium ethoxide, alkali metal hydroxides such as sodium hydroxide and potassium hydroxide, and carbonates such as sodium carbonate and potassium carbonate.

Also, this reaction may be carried out in an inert solvent, e.g., an alcohol such as methanol or ethanol, an ether such as dioxane or tetrahydrofuran, an aromatic hydrocarbon such as benzene, toluene or xylene, a nitrile such as acetonitrile, an amide such as dimethylformamide or dimethylacetamide, or a sulfoxide such as dimethylsulfoxide.

Reaction temperature is normally 10° to 200° C., preferably 50° to 100° C. Reaction time is normally 30 minutes to 24 hours, preferably 1 to 6 hours.

The compound [I] of the present invention or a salt thereof can also be prepared by carrying out a reaction (B) between a compound represented by the formula:

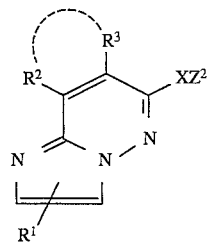 [IV]

wherein $Z^2$, $R^1$, $R^2$, $R^3$ and X are as described above, or a salt thereof, and a compound represented by the formula:

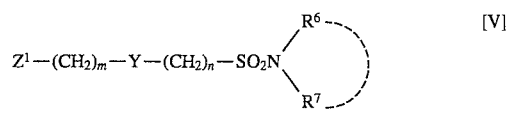 [V]

wherein $Z^1$, Y, $R^6$, $R^7$, m and n are as described above, or a salt thereof.

In this reaction, compound [V] or a salt thereof is used at normally 1 to 5 mol preferably 1 to 2 mol per mol of compound [IV] or a salt thereof.

In this reaction, it is recommended that condensation be carried out in the presence of a base. Example bases include alkali metal hydrides such as sodium hydride and potassium hydride, alkali metal alkoxides such as sodium methoxide and sodium ethoxide, alkali metal hydroxides such as sodium hydroxide and potassium hydroxide, and carbonates such as sodium carbonate and potassium carbonate.

Also, this reaction may be carried out in an inert solvent, e.g., an alcohol such as methanol or ethanol, an ether such as dioxane or tetrahydrofuran, an aromatic hydrocarbon such as benzene, toluene or xylene, a nitrile such as acetonitrile, an amide such as dimethylformamide or dimethylacetamide, or a sulfoxide such as dimethylsulfoxide.

Reaction temperature is normally 10° to 200° C., preferably 50° to 150° C. Reaction time is normally 30 minutes to 24 hours, preferably 1 to 10 hours.

Compound [I] of the present invention or a salt thereof can also be prepared by carrying out a reaction (C) between a compound represented by the formula:

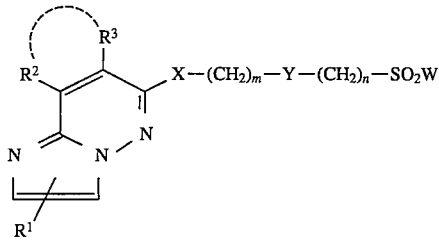

wherein W, $R^1$, $R^2$, $R^3$, X, Y, m and n are as described above, or a salt thereof, and a compound represented by the formula:

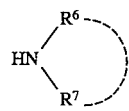

wherein $R^6$ and $R^7$ are as described above, or a salt thereof.

The splitting group represented by W is exemplified by halogen (e.g., chlorine, bromine, iodine and so on), $C_{6-10}$ arylsulfonyloxy (e.g., benzenesulfonyloxy, p-tolylsulfonyloxy and so on) and $C_{1-4}$ alkylsulfonyloxy (e.g., methanesulfonyloxy and so on), with preference given to halogen (e.g., chlorine, bromine, iodine and so on), for instance.

In this reaction, compound [VII] or a salt thereof is used at normally 1 to 5 mol, preferably 1 to 2 mol per mol of compound [VI] or a salt thereof.

Also, this reaction may be carried out in an inert solvent, e.g., an alcohol such as methanol or ethanol, an ether such as dioxane or tetrahydrofuran, an aromatic hydrocarbon such as benzene, toluene or xylene, a nitrile such as acetonitrile, an amide such as dimethylformamide or dimethylacetamide, or a sulfoxide such as dimethylsulfoxide.

Reaction temperature is normally –20° to 100° C., preferably –10° to 50° C. Reaction time is normally 30 minutes to 5 hours, preferably 1 to 3 hours.

The compound [I] or a salt thereof, thus obtained, can be converted to a salt in accordance with a conventional method when it is a free form, or to a free form or another salt in accordance with a conventional method when it is in the form of a salt. The thus obtained compound [I] or a salt thereof can be isolated and purified by known means such as solvent extraction, liquid conversion, redissolution, salting-out, crystallization, recrystallization and chromatography. When compound [I] or the salt thereof is an optically active configuration, it can be divided into the d- and l-configurations by an ordinary means of optical resolution.

Methods of producing starting material compounds [II], [III], [IV], [V], [VI] and [VII] or salts thereof used to produce compound [I] or a salt thereof are described below.

Usable salts of these compounds include salts with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid). Provided that these compounds have an acidic group as a substituent, such as —COOH, they may form a salt with an inorganic base (e.g., an alkali metal such as sodium, potassium, calcium or magnesium, an alkaline earth metal or ammonia) or an organic base (e.g., a tri-$C_{1-3}$ alkylamine such as triethylamine).

Starting material compound [II] or a salt thereof can be synthesized by, e.g., the method described in the Journal of Organic Chemistry, Vol. 39, page 2143 (1987) or analogous method based thereon.

Starting material compound [III] or a salt thereof and starting material compound [V] or a salt thereof can be synthesized by, e.g., the method described in Chemische Berichte, Vol. 91, page 2130 (1958), the Journal of Organic Chemistry, Vol. 52, page 2162 (1987), EP-A-381132 and other publications, or analogous method based thereon.

Starting material compound [IV] or a salt thereof can be synthesized by, e.g., the method described in EP-A-381132 and other publications, or analogous method based thereon.

Starting material compound [VI] or a salt thereof can be synthesized by, e.g., carrying out a reaction (1) between compound [II] or a salt thereof and a compound represented by the formula:

$$Z^2X\text{-}(CH_2)_m\text{-}Y\text{-}(CH_2)_n\text{-}SO_2W \qquad [VIII]$$

wherein X, Y, $Z^2$, W, m and n are as described above, or a reaction (2) between compound [IV] or a salt thereof and a compound represented by the formula:

$$Z^1\text{-}(CH_2)_m\text{-}Y\text{-}(CH_2)_n\text{-}SO_2W \qquad [IX]$$

wherein Y, $Z^1$, W, m and n are as described above.

In the above reaction (1), compound [VIII] is used at normally 1 to 5 mol, preferably 1 to 2 mol per mol of compound [II] or a salt thereof. This reaction can be carried out in the same manner as for the above-described reaction between compound [II] or a salt thereof and compound [III] or a salt thereof.

In the above reaction (2), compound [IX] is used at normally 1 to 5 mol, preferably 1 to 2 mol per mol of compound [IV] or a salt thereof. This reaction can be carried out in the same manner as for the above-described reaction between compound [IV] or a salt thereof and compound [V] or a salt thereof.

Starting material compound [VII] or a salt thereof, starting material compound [VIII] and starting material compound [IX] or a can be synthesized by a known method or analogous method based thereon.

These compounds or salts thereof thus obtained can be isolated and purified by known means such as solvent extraction, liquid conversion, redissolution, salting-out, crystallization, recrystallization and chromatography, but may be used as such in the form of a reaction mixture as starting materials in the following process.

In any of the above-described reactions for the compound of the present invention or starting material compounds, the substituent amino group, carboxyl group or hydroxyl group, if any, in the starting material compound, may have an introduced protecting group as commonly used in peptide chemistry and other fields; the desired compound can be obtained by removing the protecting group after reaction as necessary.

Examples of amino protecting groups include formyl, $C_{1-6}$ alkylcarbonyl (e.g., acetyl, ethylcarbonyl), phenylcarbonyl, $C_{1-6}$ alkyloxycarbonyl (e.g., methoxycarbonyl, ethoxycarbonyl), phenyloxycarbonyl, $C_{7-10}$ aralkyl-carbonyls (e.g., benzylcarbonyl), tolytyl, phthaloyl and N,N-dimethylaminomethylene which may be substituted. Example substituents for these groups include a halogen atom (e.g., fluoro, chloro, bromo, iodo), $C_{1-6}$ alkyl-carbonyl (e.g., methylcarbonyl, ethylcarbonyl, butylcarbonyl) and nitro group, the number of substituents being about 1 to 3.

Examples of carboxyl protecting groups include a $C_{1-6}$ alkyl (e.g., methyl, ethyl, n-propyl, isopropyl, n-butyl, tert-butyl), phenyl, trityl and silyl which may be substituted. Example substituents for these groups include a halogen atom (e.g., fluoro, chloro, bromo, iodo), formyl, $C_{1-6}$ alkylcarbonyl (e.g., acetyl, ethylcarbonyl, butylcarbonyl) and nitro groups, the number of substituents being about 1 to 3.

Examples of hydroxyl protecting groups include a $C_{1-6}$ alkyl (e.g., methyl, ethyl, n-propyl, isopropyl, n-butyl, tert-butyl), phenyl, $C_{7-10}$ aralkyls (e.g., benzyl), $C_{1-6}$ alkylcarbonyl (e.g. formyl, acetyl, ethylcarbonyl), phenyloxycarbonyl, $C_{7-10}$ aralkyl-carbonyl (e.g., benzylcarbonyl), pyranyl, furanyl and silyl which may be substituted. Example substituents for these groups include a halogen atom (e.g., fluoro, chloro, bromo, iodo), $C_{1-6}$ alkyl, phenyl (e.g., methyl, ethyl, n-propyl and so on), $C_{7-10}$ aralkyl (e.g., benzyl and so on) and nitro group, the number of substituents being about 1 to 4.

For removing protecting groups, known methods or analogous methods based thereon can be used, using acid, base, reducing agent, ultraviolet rays, hydrazine, phenylhydrazine, sodium N-methyldithiocarbamate, tetrabutylammonium fluoride, or palladium acetate.

Compound [I] of the present invention or a salt thereof possesses excellent anti-PAF (platelet activating factor) activity and can be used safely as an antiasthmatic drug in mammals (e.g., humans, mice, dogs, rats, bovines). Although compound [I] of the present invention or a salt thereof may be used as such in the form of bulk powder, it is a common practice to administer it in the form of a preparation along with pharmaceutical carriers. Example preparations include tablets, capsules, granules, fine subtilaes, powders, syrups, injections and inhalations. These preparations are prepared in accordance with a conventional method. Example carriers for oral preparations include those commonly used in the pharmaceutical industry, such as starch, mannitol, crystalline cellulose and carboxymethylcellulose sodium. Example injection carriers include distilled water, physiological saline, glucose solutions and transfusions. Other additives used commonly in pharmaceutical preparations may be added as appropriate. Although the dose of these preparations varies depending on age, body weight, symptoms, route and frequency of administration and other factors, it is recommended that they be administered at 0.1 to 100 mg/kg, preferably 1 to 50 mg/kg, more preferably 1 to 10 mg/kg, in one to two portions daily for an adult. Route of administration may be oral or parenteral.

EXAMPLES

The present invention is hereinafter described in more detail by means of the following Reference Examples, Examples, Preparation Examples and Experimental Examples. These examples are not to be construed as limitative.

In the Examples below, the fraction containing the desired product was detected by observation via TLC (thin-layer chromatography). TLC was conducted on a TLC plate of Merck $60F_{254}$, using a UV detector. Further, room temperature means 15° to 20° C.

Abbreviations used in the following have the following meanings.

J : coupling constant
s : singlet
bs : broad singlet
t : triplet
m : multiplet
Hz : hertz
d : doublet
q : quartet
NMR : Nuclear Magnetic Resonance
DMSO : Dimethyl sulfoxide
$CDCl_3$ : deuteriochloroform
v/v : volume/volume
% : weight %
m.p. : melting point
i.v. : intravenous injection
δ (ppm): chemical shift (part per million)

Reference Example 1

Production of ethyl 4-chloro-2,2-dimethylbutyrate

To a solution of 22.2 ml of diisopropylamine in 150 ml of tetrahydrofuran being stirred, 93.6 ml of a 1.6 M solution of n-butyl lithium in hexane was added at −5° to 0° C., followed by stirring for 30 minutes. After the reaction mixture was cooled to −78° C. and 19.0 ml of ethyl isobutyrate was added dropwise to the mixture and stirred for 45 minutes. A solution of 11.9 ml of 1-bromo-2-chloroethane in 10 ml of tetrahydrofuran was added dropwise to the reaction mixture. After the reaction mixture was stirred at −78° C. for 1 hour and then at room temperature (15° to 20° C.) for 2 hours, an excess amount of an aqueous solution of ammonium chloride was added, followed by extraction with ethyl acetate. After the extract was washed with water and dried over $MgSO_4$, the solvent was distilled off; the residue was then distilled under reduced pressure, to yield 24.7 g of the title compound in the form of a colorless oily substance.

Boiling point: 54° to 56° C./0.25 mmHg

NMR $(CDCl_3)$δ: 1.22 (6H, s), 1.26 (3H, t, J= 7.0 Hz), 2.06 (2H, t, J=8.1 Hz), 3.51 (2H, t, J=8.1 Hz), 4.14 (2H, q, J= 7.0 Hz)

Reference Example 2

Production of ethyl 2,2-dimethyl-4-thiocyanobutyrate 22.1 g of ethyl 4-chloro-2,2-dimethylbutyrate and 14.5 g of potassium thiocyanate were dissolved in 100 ml of dimethylformamide, followed by stirring at 100° C. for 7 hours. The reaction mixture was added to 500 ml of water and extracted with ethyl ether. After the extract was washed with water and dried over $MgSO_4$, the solvent was distilled off. The residue was distilled under reduced pressure to yield 16.4 g of the title compound in the form of a colorless oily substance.

Boiling point: 109° to 111° C./0.3 mmHg

NMR $(CDCl_3)$δ: 1.24 (6H, s), 1.27.(3H, t, J= 7.2 Hz), 2.00–2.12 (2H, m), 2.86–2.97 (2H, m), 2.86–2.97 (2H, m), 4.15 (2H, q, J= 7.2 Hz)

Reference Example 3

Production of ethyl 4-aminosulfonyl-2,2-dimethylbutyrate 42.5 g of ethyl 2,2-dimethyl-4-thiocyanobutyrate was dissolved in a mixture of 200 ml of acetic acid and 200 ml of water, and chlorine gas was bubbled through the solution at 10° to 15° C. for 3 hours while stirring the solution vigorously. After stirring at room temperature (15° to 20° C.) for 30 minutes, the reaction mixture was added to 500 ml of water and extracted with dichloromethane. After the extract was washed with water and dried over MgSO$_4$, the solvent was distilled off, and the residue dissolved in dichloromethane (250 ml) and ammonia gas was bubbled through the solution at 10° to 15° C. for 2 hours. After the insoluble substances were filtered off and the filtrate was washed with water and dried over MgSO$_4$, the solvent was distilled off. The residue was subjected to silica gel column chromatography and eluted with hexane:ethyl acetate (3:1) to yield 40.7 g of the title compound in the form of a colorless oily substance.

NMR (CDCl$_3$)δ: 1.23 (6H, s), 1.26 (3H, t, J= 7.2 Hz), 2.00–2.13 (2H, m), 3.06–3.19 (2H, m), 4.14 (2H, q, J= 7.2 Hz), 4.86 (2H, br)

Reference Example 4

Production of 4-hydroxy-3,3-dimethyl-1-butanesulfonamide

To a suspension of 0.35 g of lithium aluminum hydride in 30 ml of tetrahydrofuran being stirred under ice cooling conditions, a solution of 1.5 g of ethyl 4-aminosulfonyl-2,2-dimethylbutyrate in 8 ml of tetrahydrofuran was added dropwise, followed by stirring at 0° C. for 30 minutes and then at room temperature (15° to 20° C.) for 30 minutes. To the reaction mixture was added aqueous tetrahydrofuran to decompose excess lithium aluminum hydride, followed by neutralization with 2 N hydrochloric acid and extraction with ethyl acetate. After the extract was washed with water and dried over MgSO$_4$, the solvent was distilled off. The residue was subjected to silica gel column chromatography and eluted with hexane:ethyl acetate (1:1) to yield 0.94 g of the title compound.

Melting point: 75° to 76° C.

Elemental analysis (for C$_6$H$_{15}$NO$_3$S):

Calculated (%): C, 39.75; H, 8.34; N, 7.73

Found (%) : C, 39.80; H, 8.10; N, 7.92

Reference Example 5

Production of 4-(N,N-dimethylaminomethylene)aminosulfonyl-2,2-dimethyl-1-butanol To a suspension of 2.3 g of 4-hydroxy-3,3-dimethyl-1-butanesulfonamide in 40 ml of toluene, 1.59 g of N,N-dimethylformamido dimethylacetal was added, followed by stirring at 70° C. for 40 minutes. The solvent was distilled off under reduced pressure, and the residue was recrystallized from ethyl ether, to yield 2.86 g of the title compound.

NMR (CDCl$_3$)δ: 0.91 (6H, s), 1.69–1.84 (2H, m), 1.94 (1H, t, J= 4.8 Hz), 2.98–3.11 (2H, m), 3.05 (3H, s), 3.14 (3H, s), 3.34 (2H, d, J= 4.8 Hz), 8.05 (1H, s).

Reference Example 6

Production of ethyl 5-bromo-2,2-dimethylvalerate

To a solution of 28.7 ml of diisopropylamine in 150 ml of tetrahydrofuran being stirred, 126 ml of a 1.6 M solution of n-butyl lithium in hexane was added at −5° to 0° C., followed by stirring for 30 minutes. After the reaction mixture was cooled to −78° C. and 26.7 ml of ethyl isobutyrate was added dropwise to the mixture and stirred for 1 hour. 41.8 g of 1,3-dibromopropane was added dropwise to the reaction mixture. After stirring at −78° C. for 1 hour and then at room temperature (15° to 20° C.) for 2 hours, the reaction mixture was added to an aqueous solution of ammonium chloride and extracted with ethyl acetate. After the extract was washed with water and dried, the solvent was distilled off, and the residue was distilled under reduced pressure, to yield 40.3 g of the title compound in the form of a colorless oily substance.

Boiling point: 76° to 78° C./0.27 mmHg

NMR (CDCl$_3$)δ: 1.19 (6H, s), 1.25 (3H, t, J= 7.2 Hz), 1.31–1.60 (4H, m), 3.30–3.50 (2H, m), 4.12 (2H, q, J= 7.2 Hz)

Reference Example 7

Production of ethyl 6-bromo-2,2-dimethylhexanate

Using ethyl isobutyrate and 1,4-dibromobutane, the title compound was produced in the same manner as in Reference Example 6.

Boiling point: 62° to 64° C./0.4 mmHg

NMR (CDCl$_3$)δ: 1.17 (6H, s), 1.25 (3H, t, J= 7.2 Hz), 1.33–1.63 (4H, m), 3.33–3.50 (4H, m), 4.12 (2H, q, J= 7.2 Hz).

Reference Example 8

Production of ethyl 4-chloro-2,2-diethylbutyrate

Using ethyl 2-ethylbutyrate and 1-bromo-2-chloroethane, the title compound was produced in the same manner as in Reference Example 6.

Boiling point: 69° to 72° C./0.3 mmHg

NMR (CDCl$_3$)δ: 0.81 (6H, t, J= 7.1 Hz), 1.26 (3H, t, J= 7.2 Hz), 1.61 (4H, q, J= 7.2 Hz), 2.07 (2H, t, J= 8.6 Hz), 3.45 (2H, t, J= 8.6 Hz), 4.15 (2H, q, J =7.1 Hz)

Reference Example 9

Production of ethyl 5-bromo-2,2-diethylvalerate

Using ethyl 2-ethylbutyrate and 1,3-dibromopropane, the title compound was produced in the same manner as in Reference Example 6.

Boiling point: 98° to 102° C./0.3 mmHg

NMR (CDCl$_3$)δ: 0.79 (6H, t, J= 7.4 Hz), 1.25 (3H, t, J= 7.0 Hz), 1.51–1.86 (8H, m), 3.39 (2H, t, J= 6.2 Hz), 4.14 (2H, q, J= 7.0 Hz)

Reference Example 10

Production of ethyl 6-bromo-2,2-diethylhexanate

Using ethyl 2-ethylbutyrate and 1,4-dibromobutane, the title compound was produced in the same manner as in Reference Example 6.

Boiling point: 125° to 130° C./0.3 mmHg

NMR (CDCl$_3$)δ: 0.80 (6H, t, J= 7.6 Hz), 1.27 (3H, t, J= 7.0Hz), 1.49–1.78 (4H, m), 1.61 (4H, q, J= 7.6 Hz), 2.90–3.02 (2H, m), 4.15 (2H, q, J= 7.0 Hz)

Reference Example 11

Production of ethyl 2,2-dimethyl-5-thiocyanovalerate 40.3 g of ethyl 5-bromo-2,2-dimethylvalerate as obtained in Reference Example 6 and 18.2 g of potassium thiocyanate were dissolved in 120 ml of dimethylformamide, followed by stirring at 85° C. for 5 hours. The reaction mixture was added to 500 ml of water and extracted with ethyl ether. After the extract was washed with water and dried, the solvent was distilled off. The residue was distilled under reduced pressure to yield 35.7 g of the title compound in the form of an oily substance.

Boiling point: 116° to 118° C./0.3 mmHg

Reference Example 12

Production of ethyl 2,2-dimethyl-6-thiocyanohexanate

Using ethyl 6-bromo-2,2-dimethylhexanate as obtained in Reference Example 7 and potassium thiocyanate, the title compound was produced in the same manner as in Reference Example 11.

Boiling point: 123° to 125° C./0.4 mmHg

NMR (CDCl$_3$)$\delta$: 1.17 (6H, s), 1.25 (3H, t, J= 7.2 Hz), 1.33–1.65 (4H, m), 1.73–2.08 (2H, m), 2.94 (2H, t, J= 7.2 Hz), 4.12 (2H, q, J= 7.2 Hz)

Reference Example 13

Production of ethyl 2,2-diethyl-4-thiocyanobutyrate

Using ethyl 4-chloro-2,2-diethylbutyrate as obtained in Reference Example 8 and potassium thiocyanate, the title compound was produced in the same manner as in Reference Example 11.

Boiling point: 105° to 108° C./0.3 mmHg

NMR (CDCl$_3$)$\delta$: 0.81 (3H, t, J= 7.4 Hz), 0.83 (3H, t, J= 7.4 Hz), 1.27 (3H, t, J=7.0 Hz), 1.54–1.72 (4H, m), 2.00–2.13 (2H, m), 2.80–2.92 (2H, m), 4.17 (2H, q, J= 7.0 Hz)

Reference Example 14

Production of ethyl 2,2-diethyl-5-thiocyanovalerate

Using ethyl 5-bromo-2,2-diethylvalerate as obtained in Reference Example 9 and potassium thiocyanate, the title compound was produced in the same manner as in Reference Example 11.

Boiling point: 125° to 130° C./0.3 mmHg

NMR (CDCl$_3$)$\delta$: 0.80 (6H, t, J=7.6 Hz), 1.27 (3H, t, J= 7.0 Hz), 1.49–1.78 (4H, m), 1.61 (4H, q, J= 7.6 Hz), 2.90–3.02 (2H, m), 4.15 (2H, q, J= 7.0 Hz)

Reference Example 15

Production of ethyl 2,2-diethyl-6-thiocyanohexanate

Using ethyl 6-bromo-2,2-diethylhexanate as obtained in Reference Example 10 and potassium thiocyanate, the title compound was produced in the same manner as in Reference Example 11.

Boiling point: 145° to 148° C./0.3 mmHg

NMR (CDCl$_3$)$\delta$: 0.78 (6H, t, J= 7.6 Hz), 1.25 (3H, t, J= 7.0 Hz), 1.21–1.68 (8H, m), 1.82 (2H, m), 2.95 (2H, t, J= 7.4 Hz), 4.14 (2H, q, J= 7.0 Hz)

Reference Example 16

Production of ethyl 5-aminosulfonyl-2,2-dimethylvalerate 35.68 g of ethyl 2,2-dimethyl-5-thiocyanovalerate as obtained in Reference Example 11 was dissolved in a mixture of 150 ml of acetic acid and 150 ml of water, and chlorine gas was bubbled through the solution at 10° to 15° C. for 1.2 hours while stirring vigorously. After stirring at 0° C. for 1 more hour, the reaction mixture was extracted with dichloromethane. After the extract was washed with water and dried, the solvent was distilled off. The residue was then dissolved in 200 ml of dichloromethane, and ammonia gas was bubbled through the solution at 0° C. for 40 minutes. After insoluble substances were filtered off and the filtrate was washed with water and dried, the solvent was distilled off. The residue was subjected to column chromatography using 150 g of silica gel and eluted with ethyl acetate:hexane (1:1) to yield 30 g of the title compound.

NMR (CDCl$_3$)$\delta$: 1.20 (6H, s), 1.26 (3H, t, J= 7.4 Hz), 1.61–1.93 (4H, m), 3.11 (2H, t, J= 7.0 Hz), 4.14 (2H, q, J= 7.4 Hz), 4.88 (2H, bs)

Reference Example 17

Production of ethyl 6-aminosulfonyl-2,2-dimethylhexanate

Using ethyl 2,2-dimethyl-6-thiohexanate as obtained in Reference Example 12, the title compound was produced in the same manner as in Reference Example 16.

NMR (CDCl$_3$)$\delta$: 1.17 (6H, s), 1.25 (3H, t, J= 7.2 Hz), 1.32–1.64 (4H, m), 1.85 (2H, t, J= 7.6 Hz), 3.12 (2H, t, J= 7.6 Hz), 4.12 (2H, q, J=7.2 Hz), 4.84 (2H, bs)

Reference Example 18

Production of ethyl 4-aminosulfonyl-2,2-diethylbutyrate

Using ethyl 2,2-diethyl-4-thiocyanobutyrate as obtained in Reference Example 13, the title compound was produced in the same manner as in Reference Example 16.

Melting point: 93° to 94° C.

Elemental analysis (for C$_{10}$H$_{21}$NO$_4$S):

Calculated (%): C, 47.79; H, 8.42; N, 5.57

Found (%) : C, 47.73; H, 8.44; N, 5.70

NMR (CDCl$_3$)$\delta$: 0.83 (6H, t, J= 7.4 Hz), 1.27 (3H, t, J= 7.0 Hz), 1.61 (4H, q, J= 7.4 Hz), 2.03–2.16 (2H, m), 2.99–3.13 (2H, m), 4.17 (2H, q, J= 7.0 Hz), 4.84 (2H, bs)

Reference Example 19

Production of ethyl 5-aminosulfonyl-2,2-diethylvalerate

Using ethyl 2,2-diethyl-5-thiocyanovalerate as obtained in Reference Example 14, the title compound was produced in the same manner as in Reference Example 16.

Melting point: 66° to 67° C.

Elemental analysis (for C$_{11}$H$_{23}$NO$_4$S):

Calculated (%): C, 49.79; H, 8.74; N, 5.28

Found (%) : C, 49.43; H, 8.81; N, 5.18

NMR (CDCl$_3$)δ: 0.79 (6H, t, J= 7.4 Hz), 1.26 (3H, t, J= 7.2 Hz), 1.61 (4H, q, J= 7.4 Hz), 1.66–1.85 (4H, m), 3.11 (2H, t, J= 6.6 Hz), 4.15 (2H, q, J= 7.2 Hz), 4.84 (2H, bs)

Reference Example 20

Production of ethyl 6-aminosulfonyl-2,2-diethylhexanate

Using ethyl 2,2-diethyl-6-thiocyanohexanate as obtained in Reference Example 15, the title compound was produced in the same manner as in Reference Example 16.

NMR (CDCl$_3$)δ: 0.77 (6H, t, J= 7.4 Hz), 1.25 (3H, t, J= 7.2 Hz), 1.19–1.40 (2H, m), 1.58 (4H, q, J= 7.4 Hz), 1.49–1.69 (2H, m), 1.85 (2H, m), 3.12 (2H, m), 4.13 (2H, q, J= 7.2 Hz), 4.71 (2H, bs)

Reference Example 21

Production of 5-hydroxy-4,4-dimethyl-1-pentanesulfonamide

To a suspension of 1.71 g of lithium aluminum hydride in 100 ml of tetrahydrofuran being stirred under ice cooling conditions, a solution of 7.1 g of ethyl 5-aminosulfonyl-2, 2-dimethylvalerate as obtained in Reference Example 16 in 20 ml of tetrahydrofuran was added dropwise, followed by stirring at 0° C. for 40 minutes. To the reaction mixture was added aqueous tetrahydrofuran to decompose excess lithium aluminum hydride, followed by neutralization with 2 N hydrochloric acid and extraction with ethyl acetate. After the extract was washed with water and dried, the solvent was distilled off. The residue was subjected to silica gel column chromatography using 100 g of silica gel and eluted with hexane:ethyl acetate (4:1) to yield 3.39 g of the title compound in the form of an oily substance.

NMR (CDCl$_3$)δ: 0.90 (6H, s), 1.35–1.50 (2H, m), 1.75–1.97 (2H, m), 3.12 (2H, t, J= 7.8 Hz), 3.35 (2H, s), 5.04 (2H, bs)

Reference Example 22

Production of 6-hydroxy-5,5-dimethyl-1-hexanesulfonamide

Using ethyl 6-aminosulfonyl-2,2-dimethylhexanate as obtained in Reference Example 17, the title compound was produced in the same manner as in Reference Example 21.

NMR (CDCl$_3$)δ: 0.87 (6H, s), 1.21–1.54 (4H, m), 1.76–1.94 (2H, m), 2.05 (1H, s), 3.16 (2H, t, J= 8 Hz), 3.31 (2H, s), 5.13 (2H, bs)

Reference Example 23

Production of 4-hydroxy-3,3-diethyl-1-butanesulfonamide

Using ethyl 4-aminosulfonyl-2,2-diethylbutyrate as obtained in Reference Example 18, the title compound was produced in the same manner as in Reference Example 21.

Melting point: 79° to 80° C.

Elemental analysis (for $C_8H_{19}NO_3S$):

Calculated (%): C, 45.91; H, 9.15; N, 6.69

Found (%) : C, 46.00; H, 9.20; N, 6.69

NMR (CDCl$_3$)δ: 0.74 (6H, t, J= 7.4 Hz), 1.58 (4H, q, J= 7.4Hz), 1.50–1.66 (2H, m), 2.83–2.97 (2H, m), 3.11 (2H, s), 6.71 (2H, bs)

Reference Example 24

Production of 5-hydroxy-4,4-diethyl-1-pentanesulfonamide

Using ethyl 5-aminosulfonyl-2,2-diethylvalerate as obtained in Reference Example 19, the title compound was produced in the same manner as in Reference Example 21.

NMR (CDCl$_3$)δ: 0.79 (6H, t, J= 7.6 Hz), 1.14–1.45 (6H, m), 1.70–1.89 (2H, m), 2.05 (1H, s), 3.12 (2H, t, J= 7.6 Hz), 3.39 (2H, s), 5.13 (2H, bs)

Reference Example 25

Production of 6-hydroxy-5,5-diethyl-1-hexanesulfonamide

Using ethyl 6-aminosulfonyl-2,2-diethylhexanate as obtained in Reference Example 20, the title compound was produced in the same manner as in Reference Example 21.

Melting point: 64° to 65° C.

Elemental analysis (for $C_{10}H_{23}NO_3S$):

Calculated (%): C, 50.60; H, 9.77; N, 5.90

Found (%) : C, 50.90; H, 9.58; N, 6.15

NMR (CDCl$_3$)δ: 0.78 (6H, t, J= 7.2 Hz), 1.15–1.49 (4H, m), 1.23 (4H, q, J =7.2 Hz), 1.67 (1H, s), 1.85 (2H, m), 3.15 (2H, t, J= 4.6 Hz), 3.35 (2H, s) 4.90 (2H, bs)

Reference Example 26

Production of 4-(N,N-dimethylaminomethylene)aminosulfonyl-2,2 -diethyl-1-butanol To a solution of 2.0 g of 4-hydroxy-3,3-diethyl-1-butane-sulfonamide as obtained in Reference Example 23 in 30 ml of toluene, 1.2 g of N,N-dimethylformamido dimethylacetal was added, followed by stirring at 90° C. for 1 hour. The solvent was distilled off under reduced pressure, and the residue subjected to column chromatography using 70 g of silica gel and eluted with ethyl acetate:chloroform:methanol (20:20:1) to yield 2.43 g of the title compound in the form of an oily substance.

NMR (CDCl$_3$)δ: 0.81 (6H, t, J= 7.4 Hz), 1.15–1.38 (4H, m), 1.68–1.80 (2H, m), 1.96 (1H, bs), 2.96–3.07 (2H, m), 3.04 (3H, s), 3.14 (3H, s), 3.36 (2H, s), 8.05(1H, s)

Reference Example 27

Production of 5-(N,N-dimethylaminomethylene)aminosulfonyl-2,2 -diethyl-1-pentanol Using 5-hydroxy-4,4-diethyl-1-pentanesulfonamide as obtained in Reference Example 24, the title compound was produced in the same manner as in Reference Example 26.

Melting point: 87° to 88° C.

Elemental analysis (for $C_{12}H_{26}N_2O_3S$):

Calculated (%): C, 51.77; H, 9.41; N, 10.06

Found (%) : C, 51.75; H, 9.47; N, 10.09

NMR (CDCl$_3$)δ: 0.78 (6H, t, J= 7.4 Hz), 1.18–1.41 (6H, m), 1.64 (1H, s), 1.70– 1.85 (2H, m), 2.99 (2H, t, J= 7.6 Hz), 3.04 (3H, s), 3.14 (3H, s), 3.37 (2H, s), 8.04 (1H, s)

Reference Example 28

Production of 2-isopropyl-1,3-propanediol

To a suspension of 4.17 g of lithium aluminum hydride in tetrahydrofuran being stirred under ice cooling conditions, 15 g of diethyl isopropylmalonate was added dropwise, followed by reaction mixture stirring at 0° C. for 30 minutes and then at room temperature (15° to 20° C.) for 1 hour. To the reaction mixture was added aqueous tetrahydrofuran to decompose excess lithium aluminum hydride, followed by neutralization with 6 N hydrochloric acid; the insoluble substances were filtered off. The filtrate was extracted with ethyl acetate, and the extract was washed with water and dried. The solvent was distilled off under reduced pressure to yield 7.47 g of title compound.

NMR (CDCl$_3$)δ: 0.92 (3H, s), 0.95 (3H, s), 1.49–1.65 (1H, m), 1.66–1.86 (1H, m), 2.32 (2H, bs), 3.72–3.93 (4H, m)

Reference Example 29

Production of 2-ethyl-2-methyl-1,3-propanediol

Using diethyl 2-ethyl-2-methylmalonate, the title compound was produced in the same manner as in Reference Example 28.

Boiling point: 78° to 81° C./0.3 mmHg

NMR (CDCl$_3$)δ: 0.81 (3H, s), 0.87 (3H, t, J= 7.2 Hz), 1.38 (2H, q, J= 7.2 Hz), 2.48 (2H, bs), 3.54 (4H, s)

Reference Example 30

Production of 3-bromo-2-isopropyl-1-propanol 11.8 g of 2-isopropyl-1,3-propanediol as obtained in Reference Example 28 was dissolved in 150 ml of dichloromethane. To this solution was added 26 g of triphenylphosphine, and 17.8 g of N-bromosuccinimide was added in small portions under ice cooling conditions. The reaction mixture was stirred with ice cooling for 30 minutes and then at room temperature (15° to 20° C.) for 1 hour. After reaction mixture concentration under reduced pressure, the residue was subjected to column chromatography using 100 g of silica gel and eluted with ethyl acetate:hexane (3:7) to yield 11.87 g of the title compound in the form of an oily substance.

NMR (CDCl$_3$)δ: 0.94 (3H, s), 0.98 (3H, s), 1.40–1.69 (2H, m), 1.71–1.93 (1H m), 3.61–3.92 (4H, m)

Reference Example 31

Production of 3-bromo-2-ethyl-2-methyl-1-propanol

Using 2-ethyl-2-methyl-1,3-propanediol as obtained in Reference Example 29, the title compound was produced in the same manner as in Reference Example 30. NMR (CDCl$_3$)δ: 0.87 (3H, t, J= 7.4 Hz), 0.96 (3H, s), 1.40 (2H, q, J= 7.4 Hz), 1.53 (1H, bs), 3.40 (2H, s), 3.48 (2H, s)

Reference Example 32

Production of 3-acetoxy-2-isopropyl-1-propanethiocyanate

A mixture of 22 g of 3-bromo-2-isopropyl-1-propanol, 16.5 g of potassium thiocyanate and 100 ml of dimethylformamide was stirred at 100° C. for 15 hours. After cooling the reaction mixture, a mixture of 200 ml of diethyl ether and 200 ml of water was added, and the organic layer was separated. The water layer was extracted with 150 ml of diethyl ether; the extracts were then combined, washed with saturated saline and dried. The solvent was distilled off under reduced pressure. To the residue were added 17.4 g of acetic anhydride and 18.3 g of pyridine, followed by stirring at room temperature (15° to 20° C.) for 3 hours. The solvent was distilled off under reduced pressure, and the residue was subjected to column chromatography using 200 g of silica gel and eluted with ethyl acetate:hexane (1:5) to yield 14.07 g of the title compound in the form of a colorless oily substance.

NMR (CDCl$_3$)δ: 0.97 (3H, d, J= 7.3 Hz); 1.01 (3H, d, J= 7.3 Hz), 1.84–2.05 (2H, m), 2.08 (3H, s), 2.97–3.24 (2H, m), 4.03–4.35 (2H, m)

Reference Example 33

Production of 3-acetoxy-2-ethyl-2-methyl-1-propanethiocyanate

Using 3-bromo-2-ethyl-2-methyl-1-propanol, the title compound was produced in the same manner as in Reference Example 32.

NMR (CDCl$_3$)δ: 0.90 (3H, t, J= 7.4 Hz), 1.03 (3H, s), 1.46 (2H, q, J= 7.4 Hz), 2.09 (3H, s), 3.07 (2H, s), 3.94 (2H, s)

Reference Example 34

Production of 3-acetoxy-2-isopropyl-1-propanesulfonamide 10 g of 3-acetoxy-2-isopropyl-1-propanethiocyanate was dissolved in a mixture of 50 ml of acetic acid and 50 ml of water. While stirring vigorously, chlorine gas was bubbled through the solution at room temperature (15° to 20° C.) for 2 hours. The reaction mixture was extracted with dichloromethane, and the extract was washed with saturated saline and dried. The solvent was distilled off under reduced pressure. The residue was dissolved in 100 ml of dichloromethane, and while maintaining a reaction temperature of under 15° C. with ice cooling, ammonia gas was bubbled to the solution for 30 minutes. After the precipitate was filtered off, the filtrate was concentrated. The residue was then subjected to column chromatography, using 100 g of silica gel, and eluted with methanol:chloroform (1:20) to yield 7.9 g of the title compound in the form of an oily substance.

NMR (CDCl$_3$)δ: 0.96 (3H, d, J= 6.8 Hz), 0.98 (3H, d, J= 6.8 Hz), 1.89–2.07 (1H, m), 2.08 (3H, s), 2.17–2.32 (1H, m), 3.11–3.19 (2H, m), 4.21–4.29 (2H, m), 4.87 (2H, bs).

Reference Example 35

Production of 3-acetoxy-2-ethyl-2-methyl-1-propanesulfonamide

Using 3-acetoxy-2-ethyl-2-methyl-1-propanethiocyanate, the title compound was produced in the same manner as in Reference Example 34.

NMR (CDCl$_3$)δ: 0.90 (3H, t, J= 7.4 Hz), 1.16 (3H, s), 1.57 (2H, q, J= 7.4 Hz), 2.09 (3H, s), 3.24 (2H, dd, J= 2.5 Hz and 4.9 Hz), 4.08 (2H, s), 4.86 (2H, bs)

Reference Example 36

Production of
3-hydroxy-2-isopropyl-1-propanesulfonamide 7.0 g of 3-acetoxy-2-isopropyl-1-propanesulfonamide was dissolved in 50 ml of methanol. While stirring the solution at room temperature (15° to 20° C.), 6.5 g of 28 w/w % sodium methoxide was added, and reaction was carried out for 30 minutes. The reaction mixture was concentrated to dryness; the residue was then subjected to column chromatography using 100 g of silica gel and eluted with chloroform:methanol (9:1) to yield 4.4 g of the title compound.

Melting point: 83° to 84° C.
Elemental analysis (for $C_6H_{15}NO_3S$):
Calculated (%): C, 39.76; H, 8.34; N, 7.73
Found (%) : C, 39.72; H, 8.36; N, 7.78
NMR ($d_6$-DMSO)δ: 0.87 (3H, d, J= 7.0 Hz), 0.87 (3H, d, J= 7.0 Hz), 1.79– 2.09 (2H, m), 2.85–2.95 (2H, m), 3.43–3.59 (2H, m), 4.55 (1H, bs), 6.77 (2H, bs)

Reference Example 37

Production of
3-hydroxy-2-ethyl-2-methyl-1-propanesulfonamide

Using 3-acetoxy-2-ethyl-2-methyl-1-propanesulfonamide, the title compound was produced in the same manner as in Reference Example 36.

NMR (CDCl$_3$)δ: 0.90 (3H, t, J= 7.4 Hz), 1.07 (3H, s), 1.33–1.68 (2H, m), 2.71 (1H, bs), 3.22 (2H, q, J= 7.4 Hz), 3.61 (2H, s), 5.13 (2H, bs)

Reference Example 38

Production of ethyl 1-(2-chloroethyl)cyclohexanate

Using ethyl cyclohexanate, the title compound was produced in the same manner as in Reference Example 1.

Boiling point: 83° to 86° C./0.25 mmHg
NMR (CDCl$_3$)δ: 1.11–1.68 (8H, m), 1.27 (3H, t, J= 7.2 Hz), 2.01 (2H, t, J= 6.7 Hz), 1.91–2.16 (2H, m), 3.45 (2H, t, J= 6.7 Hz), 4.16 (2H, q, J= 7.2 Hz)

Reference Example 39

Production of ethyl
1-(2-thiocyanoethyl)cyclohexanate

Using ethyl 1-(2-chloroethyl)cyclohexanate, the title compound was produced in the same manner as in Reference Example 2.

Boiling point: 118° to 122° C./0.25 mmHg
NMR (CDCl$_3$)δ: 1.29 (3H, t, J= 7.2 Hz), 1.14–1.66 (8H, m), 1.92–2.14 (4H, m), 2.80–2.90 (2H, m), 4.19 (2H, q, J= 7.2 Hz)

Reference Example 40

Production of ethyl
1-(2-aminosulfonylethyl)cyclohexanate

Using ethyl 1-(2-thiocyanoethyl)cyclohexanate, the title compound was produced in the same manner as in Reference Example 3.

NMR (CDCl$_3$)δ: 1.27 (3H, t, J= 7.0 Hz), 1.16– 1.71 (10H, m), 1.94–2.14 (2H, m), 2.98–3.13 (2H, m), 4.17 (2H, q, J= 7.0 Hz), 4.69 (2H, bs)

Reference Example 41

Production of
4-hydroxy-3,3-pentamethylene-1-butanesulfonamide

Using ethyl 1-(2-aminosulfonylethyl)cyclohexanate, the title compound was produced in the same manner as in Reference Example 4.

NMR (CDCl$_3$)δ: 1.19–1.56 (10H, m), 1.82–1.97 (2H, m), 2.05 (1H, s), 3.06– 3.22 (2H, m), 3.43 (2H, s), 5.27 (2H, bs)

Reference Example 42

Production of
3-(N,N-dimethylaminomethylene)aminosulfonyl-2
-isopropyl-1-propanol Using 3-hydroxy-2-isopropyl-1-propanesulfonamide, the title compound was produced in the same manner as in Reference Example 5.

NMR (CDCl$_3$)δ: 0.91 (3H, d, J= 6.6 Hz), 0.94 (3H, d, J= 6.6 Hz), 1.64 (1H, bs), 1.82–2.11 (2H, m), 3.04 (3H, s), 3.11 (2H, d, J= 6.6 HZ), 3.15 (3H, s), 3.63–3.93 (2H, m), 8.06 (1H, s)

Reference Example 43

Production of
3-(N,N-dimethylaminomethylene)aminosulfonyl-2
-ethyl-2-methyl-1-propanol Using 3-hydroxy-2-ethyl-2-methyl-1-propanesulfonamide, the title compound was produced in the same manner as in Reference Example 5.

NMR (CDCl$_3$)δ: 0.88 (3H, t, J=7.4 Hz), 1.05 (3H, s), 1.32–1.73 (2H, m), 3.04 (2H, q, J= 7.4 Hz), 3.05 (3H, s), 3.15 (3H, s), 3.56–3.69 (2H, m), 8.05 (1H, s)

Reference Example 44

Production of
4-(N,N-dimethylaminomethylene)aminosulfonyl-2,2
-pentamethylene-1-butanol Using 4-hydroxy-3,3-pentamethylene-1-butanesulfonamide, the title compound was produced in the same manner as in Reference Example 5.

NMR (CDCl$_3$)δ: 1.22–1.54 (10H, m), 1.80–1.94 (4H, m), 3.05 (3H, s), 3.14 (3H, s), 3.41 (2H, s), 8.05 (1H, s)

Reference Example 45

Production of 3-acetoxy-1-propanethiocyanate

Using 3-bromo-1-propanol in place of 3-bromo-2-isopropyl-1-propanol in reference example 32, substantially the same reaction was conducted as in reference example 32 to produce the title compound.

NMR (CDCl$_3$)δ: 2.02 (3H,s), 1.97– 2.11 (3H,m) 3.15, 4.12 (each 3H, t, J=6Hz).

Reference Example 46

Production of 3-acetoxy-1-propanesulfonylchloride

Chlorine gas was bubbled in a mixture of 73 g of 3-acetoxy-1-propanethiocyanate and 300 ml of water under ice-cooling with vigorously stirring for 5 hours. The reaction solution was extracted with dichloromethane (200 ml ×2), and the extracts were washed with a water (200 ml ×2), and dried over anhydrous magnesium sulfate. The solvent was distilled off to give 88.1 g of the title compound.

NMR (CDCl$_3$)δ: 2.09 (3H,s), 2.32–2.46 (2H,m), 3,78, 4.25 (each 3H,t,J= 6Hz).

Reference Example 47

Production of 3-acetoxy-N-methyl-1-propanesulfonamide 15 g of 3-acetoxy-1-propanesulfonylchloride was dissolved in 150 ml dichloromethane. To the mixture was added dropwise 11.6 g of methylamine (40% methanol solution) with stirring under ice coioling. The reaction mixture was stirred for 1.5 hours under ice cooling.

The reaction mixture was washed with water (150 ml ×2), dried over magnesium sulfate, the solvent was distilled off. The residue was subjected to silica gel column chromatography, eluting with dichloromethanemethanol (25:1) to give 7.73 g of the title compound.

NMR (CDCl$_3$)δ: 2.08 (3H,s), 2.11–2.22 (2H,m), 2,83 (3H,d,J=5Hz), 3.07– 3.15 (2H,m), 4.17–4.23 (3H,m)

Reference Example 48

Production of 3-hydroxy-N-methyl-1-propanesulfonamide

Using 3-acetoxy-N-methyl-1-propanesulfonamide in place of 3 -acetoxy-2-isopropyl-1-propanesulfonamide in reference example 36, substantially the same reaction was conducted as in reference example 36 to produce the title compound.

NMR (CDCl$_3$)δ: 1.69–1.90 (2H,m), 2.56 (3H,d,J=5Hz), 2.97–3.05, 3.43–3.52 (each 2H,m), 4.64 (1H,t,J=4.5Hz), 6.84–6.90 (1H, m).

Reference Example 49

Production of 3-hydroxy-N,N-dimethylpropane-1-sulfonamide

Using 3-acetoxy-1-propanesulfonylchloride and dimethylamine, substantially the same reaction was conducted as in reference example 47 and 48 to produce the title compound.

NMR (CDCl$_3$)δ: 1.91 (1H,brs), 2.0–2.2 (2H,m), 2.89 (6H,s), 3.0–3.2 (2H,m), 3.7–3.9 (2H,m).

Reference Example 50

Production of 3-(1-methyl-4-piperazinylsulfonyl)-1-propylacetate

Using N-methylpiperazine in place of methylamine in reference example 47, substantially the same reaction was conducted as in reference example 47 to produce the title compound.

NMR (CDCl$_3$)δ: 2.07, 2.33 (each 3H,s), 2.11–2.22, 2.94–3.02, 4.15–4.21 (each 2H,m), 2.47–2.51, 3.29–3.34 (each 4H,m)

Reference Example 51

Production of 3-(1-methyl-4-piperazinylsulfonyl)-1-propanol

Using 3-(1-methyl-4-piperazinylsulfonyl)-1-propylacetate in place of 3-acetoxy-2-isopropyl-1-propanesulfonamide in reference example 36, substantially the same reaction was conducted as in reference example 36 to produce the title compound. m.p. 90°–93° C.

Elemental Analysis (for C$_8$H$_{18}$N$_2$O$_3$S)

Calculated (%): C, 43.22; H, 8.16; N, 12.60

Found (%) : C, 43.01; H, 8.20; N, 12.53

Example 1

Production of 7,8-dimethyl-6-(2,2-dimethyl-3-sulfamoyl-1-propoxy)imidazo[1,2-b]pyridazine 0.59 g of 60% oily sodium hydride was suspended in 21 ml of dimethylformamide. To this suspension, 1.18 g of 3-hydroxy-2,2-dimethyl-1 -propanesulfonamide was added, followed by stirring at room temperature (15° to 20° C.) under reduced pressure for 1 hour. To this mixture was added 1.28 g of 6-chloro-7,8-dimethylimidazo[ 1,2-b]pyridazine, followed by stirring at 60° C. for 40 minutes. After dimethylformamide was distilled off under reduced pressure, ice water was added to the residue, which was subsequently adjusted to pH 6 by the addition of 5 N hydrochloric acid and then extracted with ethyl acetate-tetrahydrofuran (2:1). The extract was washed with 20 ml of saturated saline and then dried over magnesium sulfate. After the solvent was distilled off under reduced pressure, the residue was subjected to silica gel column chromatography and eluted with dichloromethane-ethyl acetate-methanol (10:10:1). The fraction containing the desired product was concentrated and recrystallized from ethanol to yield 0.866 g of the title compound.

Melting point: 222° to 225° C.

Elemental analysis (for C$_{13}$H$_{20}$N$_4$O$_3$S):

Calculated (%): C, 49.98; H, 6.45; N, 17.93

Found (%) : C, 49.73; H, 6.41; N, 17.68

Example 2

Production of 7,8-dimethyl-6-(2,2-dimethyl-3-sulfamoyl-1-propoxy)imidazo[1,2-b]pyridazine hydrochloride 0.421 g of 7,8-dimethyl-6-(2,2-dimethyl-3-sulfamoyl-1-propoxy)imidazo[ 1,2-b]pyridazine was suspended in 20 ml of ethanol. To this suspension, 1.65 ml of 1 N hydrochloric acid was added. After the resulting solution was concentrated under reduced pressure, ethyl ether was added to the residue to cause crystallization, to yield 0.45 g of the title compound.

Melting point: 218° to 220° C.

Elemental analysis (for C$_{13}$H$_{21}$ClN$_4$O$_3$S):

Calculated (%): C, 44.76; H, 6.07; N, 16.06

Found (%) : C, 44.82; H, 5.94; N, 15.93

Example 3

Production of 6-(2,2-dimethyl-3-sulfamoyl-1-propoxy)-7-methylimidazo[1,2-b]pyridazine 1.12 g of 60% oily sodium hydride was suspended in 25 ml of dimethylformamide. To this suspension, 1.51 g of 3-hydroxy-2,2-dimethyl-1-propanesulfonamide was added, followed by stirring at room temperature (15° to 20° C.) under reduced pressure for i hour. To this mixture was added 1.51 g of 6-chloro-7-methylimidazo[1,2-b]pyridazine, followed by stirring at 60° C. for 2 hours. After dimethylformamide was distilled off under reduced pressure, ice water was added to the residue, which was subsequently adjusted to pH 6 by the addition of 5 N hydrochloric acid and then extracted with tetrahydrofuran. The extract was washed with 20 ml of saturated saline and then dried over magnesium sulfate. After the solvent was distilled off under reduced pressure, the residue was subjected to silica gel column chromatography and eluted with dichloromethane-ethyl acetate-methanol (5:5:1). The fraction containing the desired product was concentrated and recrystallized by the addition of ethyl ether-ethyl acetate (5:1). The resulting crystal was collected by filtration, to yield 0.522 g of the title compound.

Melting point: 235° to 237° C.

Elemental analysis (for $C_{12}H_{18}N_4O_3S$):

Calculated (%): C, 48.31; H, 6.08; N, 18.78

Found (%) : C, 48.07; H, 6.21; N, 18.50

Example 4

Production of 6-(2,2-dimethyl-3-sulfamoyl-1-propoxy)-7-methylimidazo[1,2-b]pyridazine hydrochloride 0.503 g of 6-(2,2-dimethyl-3-sulfamoyl-1-propoxy)-7-methylimidazo[1,2-b]pyridazine was suspended in 15 ml of ethanol. To this suspension, 1.8 ml of 1 N hydrochloric acid was added. After the resulting solution was concentrated under reduced pressure, ethanol-ethyl ether (4:1) was added to the residue to cause crystallization to yield 0.533 g of the title compound.

Melting point: 216° to 217° C.

Elemental analysis (for $C_{12}H_{19}ClN_4O_3S \cdot 0.4H_2O$):

Calculated (%): C, 42.14; H, 5.84; N, 16.38

Found (%) : C, 42.29; H, 5.87; N, 16.45

Example 5

Production of 6-(2,2-dimethyl-3-sulfamoyl-1-propoxy)-8-methylimidazo[1,2-b]pyridazine 1.68 g of 6-chloro-8-methylimidazo[1,2-b]pyridazine was treated in the same manner as in Example 3 to yield 0.677 g of the title compound.

Melting point: 182° to 185° C.

Elemental analysis (for $C_{12}H_{18}N_4O_3S$):

Calculated (%): C, 48.31; H, 6.08; N, 18.78

Found (%) : C, 48.55; H, 6.17; N, 18.55

Example 6

Production of 6-(2,2-dimethyl-3-sulfamoyl-1-propoxy)-8-methylimidazo[1,2-b]pyridazine hydrochloride 0.597 g of 6-(2,2-dimethyl-3-sulfamoyl-1-propoxy)-8-methylimidazo[1,2-b]pyridazine was treated in the same manner as in Example 4 to yield 0.607 g of the title compound.

Melting point: 176° to 179° C.

Elemental analysis (for $C_{12}H_{19}ClN_4O_3S \cdot 0.6H_2O$):

Calculated (%): C, 41.70; H, 5.89; N, 16.21

Found (%) : C, 41.45; H, 5.91; N, 16.20

Example 7

Production of 6-(2,2-dimethyl-3-sulfamoyl-1-propoxy)-7,8,9,10-tetrahydroimidazo[2,1-a]phthalazine 0.59 g of 60% oily sodium hydride was suspended in 20 ml of dimethylformamide. To this suspension, 1.18 g of 3-hydroxy-2,2-dimethyl-1-propanesulfonamide was added, followed by stirring at room temperature (15° to 20° C.) under reduced pressure for 30 minutes. To this mixture was added 1.35 g of 6-chloro-7,8,9,10-tetrahydroimidazo[2,1-a]phthalazine, followed by stirring at 60° C. for 1.5 hours. After dimethylformamide was distilled off under reduced pressure, ice water was added to the residue, which was subsequently adjusted to pH 6 by the addition of 5 N hydrochloric acid and then extracted with ethyl acetate-tetrahydrofuran (2:1). The extract was washed with 20 ml of saturated saline and then dried over magnesium sulfate. After the solvent was distilled off under reduced pressure, the residue was subjected to silica gel column chromatography and eluted with dichloromethane-ethyl acetate-methanol (20:20:1). The fraction containing the desired product was concentrated, and ethyl ether was added to separate a crystal, which was collected by filtration, to yield 0.66 g of the title compound.

Melting point: 198° to 200° C.

Example 8

Production of 6-(2,2-dimethyl-3-sulfamoyl-1-propoxy)-7,8,9,10-tetrahydroimidazo[2,1-a]phthalazine hydrochloride 0.609 g of 6-(2,2-dimethyl-3-sulfamoyl-1-propoxy)-7,8,9,10-tetrahydroimidazo[2,1-a]phthalazine was treated in the same manner as in Example 4 to yield 0.649 g of the title compound.

Melting point: 223° to 225° C.

Elemental analysis (for $C_{15}H_{23}ClN_4O_3S$):

Calculated (%): C, 48.06; H, 6.18; N, 14.94

Found (%) : C, 48.00; H, 6.22; N, 14.65

Example 9

Production of 6-(2,2-dimethyl-3-sulfamoyl-1-propoxy)imidazo[2,1-a]phthalazine 0.293 g of 60% oily sodium hydride was suspended in 10 ml of dimethylformamide. To this suspension, 0.577 g of 3-hydroxy-2,2-dimethyl-1-propanesulfonamide was added, followed by stirring at room temperature (15° to 20° C.) under reduced pressure for 30 minutes. To this mixture was added 0.703 g of 6-chloroimidazo[2,1-a]phthalazine, followed by stirring at room temperature for 3 hours. After dimethylformamide was distilled off under reduced pressure, ice water was added to the residue, which was subsequently adjusted to pH 5.0 by the addition of 5 N hydrochloric acid and then extracted with ethyl acetate-tetrahydrofuran (1:1). The extract was washed with 20 ml of saturated saline and then dried over magnesium sulfate. After the solvent was distilled off under reduced pressure, the residue was subjected to silica gel column chromatography and eluted with dichloromethane-ethyl acetate-methanol (20:20:1). The fraction containing the desired product was concentrated and ethyl ether was added to separate a crystal, which was collected by filtration, to yield 0.769 g of the title compound.

Melting point: 209° to 212° C.

Elemental analysis (for $C_{15}H_{18}N_4O_3S$):

Calculated (%): C, 53.88; H, 5.43; N, 16.75

Found (%) : C, 53.26; H, 5.09; N, 16.42

Example 10

Production of 6-(2,2-dimethyl-3-sulfamoyl-1-propoxy)imidazo[2,1-a] phthalazine hydrochloride 0.669 g of 6-(2,2-dimethyl-3-sulfamoyl-1-propoxy)imidazo[2,1-a] phthalazine was treated in the same manner as in Example 4 to yield 0.702 g of the title compound.

Melting point: 210° to 211° C.

Elemental analysis (for $C_{15}H_{19}ClN_4O_3S$):

Calculated (%): C, 48.58; H, 5.16; N, 15.11

Found (%) : C, 48.26; H, 5.38; N, 14.82

Example 11

Production of 6-(2,2-dimethyl-4-sulfamoyl-1-butoxy)-7-methylimidazo[ 1,2-b ]pyridazine Using 0.84 g of 6-chloro-7-methylimidazo[1,2-b]pyridazine and 0.91 g of 4-hydroxy-3,3-dimethyl-1-butanesulfonamide, 0.41 g of title compound was obtained in the same manner as in Example 3.

Melting point: 161° to 162° C.

Elemental analysis (for $C_{13}H_{20}N_4O_3S$):

Calculated (%): C, 49.98; H, 6.45; N, 17.93

Found (%) : C, 49.63; H, 6.49; N, 17.66

Example 12

Production of 6-(2,2-dimethyl-5-sulfamoyl-1-pentyloxy)-7-methylimidazo[1,2-b]pyridazine Using 0.8 g of 6-chloro-7-methylimidazo[ 1,2-b]pyridazine and 1.1 g of 5 -hydroxy-4,4-dimethyl-1-pentanol, 0.5 g of the title compound, in the form of an oily substance, was obtained in the same manner as in Example 3, followed by the same procedure as in Example 4 to yield the hydrochloride of the title compound.

Melting point: 188° to 190° C.

Elemental analysis (for $C_{14}H_{22}N_4O_3S \cdot HCl$):

Calculated (%): C, 46.48; H, 6.39; N, 15.44

Found (%) : C, 46.18; H, 6.35; N, 15.47

Example 13

Production of 6-(2,2-dimethyl-6-sulfamoyl-1-hexyloxy)-7-methylimidazo[1,2-b]pyridazine Using 1.17 g of 6-chloro-7-methylimidazo[1,2-b]pyridazine and 1.5 g of 6-hydroxy-5,5-dimethyl-1-hexanol, 0.21 g of the title compound was obtained in the same manner as in Example 3.

Melting point: 169° to 170° C.

Elemental analysis (for $C_{15}H_{24}N_4O_3S$):

Calculated (%): C, 52.92; H, 7.11; N, 16.46

Found (%) : C, 52.65; H, 7.12; N, 16.30

Example 14

Production of 6-(2,2-diethyl-3-sulfamoyl-1-propoxy)-7-methylimidazo[1,2-b]pyridazine To a solution of 1.38 g of 3-(N,N-dimethylaminomethylene)aminosulfonyl -2,2-diethyl-1-propanol in 30 ml of tetrahydrofuran, 0.23 g of 60% oily sodium hydride was added, followed by stirring at room temperature for 1 hour. To the reaction mixture, 0.74 g of 6-chloro-7-methylimidazo [1,2-b] pyridazine was added, followed by refluxing under heating conditions for 1 hour. After cooling, the reaction mixture was neutralized with 1 N hydrochloric acid and extracted with ethyl acetate-tetrahydrofuran (1:1). After the extract was washed with water and dried over $MgSO_4$, the solvent was distilled off under reduced pressure. To the residue was added 14 ml of 6 N hydrochloric acid, followed by stirring at 110° C. for 30 minutes. After cooling, the mixture was concentrated under reduced pressure, and the residue adjusted to a pH of 7 by addition of aqueous solution of sodium hydrogen carbonate and then extracted with ethyl acetate. After saline washing, the extract was dried over magnesium sulfate. The solvent was distilled off under reduced pressure and the residue subjected to column chromatography using 100 g of silica gel, eluted with chloroform-methanol (5:1), and crystallized from a mixed solvent of methanol and ethyl acetate, to yield 1.19 g of the title compound.

Melting point: 210° to 211° C.

NMR ($d_6$-DMSO)δ: 0.87 (6H, t, J=7.4 Hz), 1.60 (4H, q, J=7.4 Hz), 2.25 (3H, s), 3.20 (2H, S), 4.27 (2H, s), 6.94 (2H, bs), 7.50 (1H, s), 7.84 (1H, s), 7.98 (1H, s).

Example 15

Production of 6-(2,2-diethyl-3-sulfamoyl-1-propoxy)-7-methylimidazo[1,2-b]pyridazine hydrochloride Using 0.5 g of 6-(2,2-diethyl-3-sulfamoyl-1-propoxy)-7-methylimidazo[ 1,2-b]pyridazine, 0.51 g of the title compound was obtained in the same manner as in Example 4.

Melting point: 224° to 225° C.

Elemental analysis (for $C_{14}H_{22}N_4O_3S \cdot HCl$):

Calculated (%): C, 46.34; H, 6.39; N, 15.44

Found (%) : C, 46.30; H, 6.49; N, 15.16

Example 16

Production of 6-(2,2-diethyl-4-sulfamoyl-1-butoxy)-7-methylimidazo[1,2-b]pyridazine Using 0.8 g of 6-chloro-7-methylimidazo[1,2-b]pyridazine and 1.45 g of 4-(N,N-dimethylaminomethylene)aminosulfonyl.2,2diethyl-1-butanol, 0.8 g of the title compound was obtained in the same manner as in Example 14.

Melting point: 158° to 159° C.

Elemental analysis (for $C_{15}H_{24}N_4O_3S$):

Calculated (%): C, 52.92; H, 7.11; N, 16.46

Found (%) : C, 52.73; H, 6.86; N, 16.22

Example 17

Production of 6-(2,2-diethyl-5-sulfamoyl-1-pentyloxy)-7-methylimidazo[1,2-b]pyridazine Using 0.8 g of 6-chloro-7-methylimidazo[1,2-b]pyridazine and 1.52 g of 5-(N,N-dimethylaminomethylene)aminosulfonyl-2,2-diethyl-1-pentanol, 0.84 g of the title compound was obtained in the same manner as in Example 14.

Melting point: 139° to 140° C.

Elemental analysis (for $C_{17}H_{28}N_4O_3S$):

Calculated (%): C, 55.41; H, 7.66; N, 15.20

Found (%) : C, 55.39; H, 7.68; N, 15.50

Example 18

Production of 6-(2,2-pentamethylene-4-sulfamoyl-1-butoxy)-7-methylimidazo[1,2-b]pyridazine Using 0.8 g of 6-chloro-7-methylimidazo[1,2-b]pyridazine and 1.52 g of 3-(N,N-dimethylaminomethylene)aminosulfonyl-2,2-pentamethylene -1-butanol, 1.05 g of the title compound was obtained in the same manner as in Example 14.

Melting point: 182° to 183° C.

Elemental analysis (for $C_{16}H_{24}N_4O_3S \cdot 0.2H_2O$):

Calculated (%): C, 48.96; H, 6.52; N, 14.27

Found (%) : C, 48.94; H, 6.66; N, 13.90

NMR ($d_6$-DMSO)δ: 1.31–1.73 (10H, m), 1.86–2.04 (2H, m), 2.38 (3H, s), 2.91– 3.06 (2H, m), 4.18 (2H, s), 6.78 (2H, bs), 8.18 (1H, d, J'2.0 Hz), 8.25 (1H, s), 8.46 (1H, d, J= 2.0 Hz).

Example 19

Production of 6-(2-isopropyl-3-sulfamoyl-1-propoxy)-7-methylimidazo [1,2-b]pyridazine hydrochloride Using 0.8 g of 6-chloro-7-methylimidazo[1,2-b]pyridazine and 1.29 g of 3-(N,N-dimethylaminomethylene)aminosulfonyl-2-isopropyl-1-propanol, 1.37 g of the title compound was obtained in the same manner as in Examples 14 and 15.

Melting point: 202° to 204° C.

Elemental analysis (for $C_{13}H_{20}N_4O_3S \cdot HCl$):

Calculated (%): C, 44.76; H, 6.07; N, 16.06

Found (%) : C, 44.45; H, 6.14; N, 15.78

Example 20

Production of 6-(2-ethyl-2-methyl-3-sulfamoyl)-1-propoxy)-7-methylimidazo[1,2-b]pyridazine Using 0.8 g of 6-chloro-7-methylimidazo[1,2-b]pyridazine and 1.29 g of 3-(N,N-dimethylaminomethylene)aminosulfonyl-2-ethyl-2-methyl-1-propanol, 0.95 g of the title compound was obtained in the same manner as in Example 14.

Melting point: 213° to 214° C.

Elemental analysis (for $C_{13}H_{20}N_4O_3S$):

Calculated (%): C, 49.98; H, 6.45; N, 17.93

Found (%) : C, 50.12; H, 6.45; N, 19.63

Example 21

Production of 7-methyl-6-[(3-sulfamoyl propyl)thio]imidazo-[1,2-b] pyridazine 502 mg of 6-chloro-7-methylimidazo[1,2-b]pyridazide, 1 ml of methyl 3-mercaptopropionate and 1.84 ml of 28% w/w sodium methoxide-methanol solution were dissolved in 20 ml of methanol and this solution was refluxed for 1.5 hours.

The mixture was distilled to remove the solvent and the residue was washed with dichloromethane. A solution of the residue and 747 mg of 3-iodopropylsulfonamide in 20 ml of tetrahydrofurane was refluxed for 1.5 hours. The solvent was distilled off and the residue was diluted with water and extracted with ethyl acetate (100 ml ×2). The extract was washed with a saturated saline (100 ml) and dried over anhydrous magnesium sulfate. The solvent was then distilled off and the residue was recrystallized tetrahydrofuran-isopropyl ether to yield 391 mg of title compound.

Melting point: 142° to 143° C.

Elemental Analysis for ($C_{10}H_{14}N_4O_2S_2$):

Calculated (%): C, 41.94; H, 4.93; N, 19.56

Found (%) : C, 42.11; H, 4.74; N, 19.93

Example 22

Production of 7-methyl-6-[(3-N-methylsulfamoylpropyl)oxy] imidazo[1,2-b]pyridazine In 20 ml of tetrahydrofuran-dimethylformamide (3:1) was suspended 144 mg of 60% sodium hydride in oil followed by addition of 551 mg of 3 -hydroxy-N-methylpropanesulfonamide and the mixture was stirred under nitrogen at room temperature for 30 minutes and at 50° C. for 30 minutes. Then, 501 mg of 6-chloro-7-methylimidazo[1,2-b]pyridazine was added and the mixture was further stirred at 50° C. for 1 hour and at 70° C. for 1 hour. Following addition of 150 ml of iced water, the reaction mixture was extracted with ethyl acetate (100 ml ×3). The extract was washed with 100 ml of saturated saline and dried over anhydrous magnesium sulfate. The solvent was then distilled off under reduced pressure and the residue was subjected to silica gel column chromatography, elution being carried out with dichloromethane-methanol (50:3). The fraction containing the desired product were pooled and concentrated. The residue was recrystallized from dichloromethane-isopropyl ether to yield 380 mg of the title compound.

Melting point: 148° to 150° C.

Elemental Analysis (for $C_{11}H_{16}N_4O_3S$)

Example 23

Production of 7-methyl-6-[3-N,N-dimethylsulfamoyl-propyl)oxy]imidazo[1,2-b]pyridazine In 20 ml of tetrahydrofuran-dimethylformamide (3:1) was suspended 110 mg of 60% sodium hydride in oil followed by addition of 460 mg of 3-hydroxy-N,N-dimethylpropanesulfonamide and the mixture was stirred under nitrogen at room temperature for 30 minutes and at 50° C. for 30 minutes. Then, 420 mg of 6-chloro-7-methylimidazo[1,2-b]pyridazine was added and the mixture was further stirred at 50° C. for 1 hour and at 70° C. for 1 hour. Following addition of 100 ml of iced water, the reaction mixture was extracted with ethylacetate (100 ml). The extract was washed with 100 ml of saturated saline and dried over anhydrous magnesium sulfate. The solvent was then distilled off under reduced pressure and the residue was subjected to silica gel column chromatography, elution being carried out with dichloromethane-methanol (19:1). The fraction containing the desired product were pooled and concentrated. The residue was recrystallized dichloromethane-isopropyl ether to yield 588 mg of the title compound.

Melting point: 153° to 155° C.

Elemental Analysis (for $C_{12}H_{18}N_4O_3S$)

Calculated (%): C, 48.31; H, 6.08; N, 18.78

Found (%) : C, 48.11; H, 6.12; N, 18.55

Example 24

Production of 7-methyl-6-[(3-(1-methyl-4-piperazinyl)sulfonylpropyl)oxy]imidazo[1,2-b]pyridazine In 20 ml of tetrahydrofuran-dimethylformamide (3:1) was suspended 110 mg of 60% sodium hydride in oil followed by addition of 611 mg of 3-(1-methyl-4-piperazinylsulfonyl)-1-propanol and the mixture was stirred under nitrogen at room temperature for 30 minutes and at 50° C. for 30 minutes. Then, 420 mg of 6-chloro-7-methylimidazo[1,2-b]pyridazine was added and the mixture was further stirred at 50° C. for 1 hour and at 70° C. for 1 hour. Following addition of 100 ml of iced water, the reaction mixture was extracted with ethylacetate (100 ml). The extract was washed with 50 ml of saturated saline and dried over anhydrous magnesium sulfate. The solvent was then distilled off under reduced pressure and the residue was subjected to silica gel column chromatography, elution being carried out with dichloromethanemethanol (50:3). The fraction containing the desired product were pooled and concentrated. The residue was recrystallized dichloromethane-isopropyl ether to obtain 447 mg of the title compound.

Melting point: 118° to 120° C.

Elemental Analysis (for $C_{15}H_{23}N_5O_3S$)

Calculated (%): C, 50.97; H, 6.56; N, 19.81

Found (%) : C, 50.97; H, 6.66; N, 19.83

Preparation Example 1

| (1) Compound of Example 1 | 10.0 mg |
| (2) Lactose | 60.0 mg |
| (3) Corn starch | 35.0 mg |
| (4) Gelatin | 3.0 mg |
| (5) Magnesium stearate | 2.0 mg |

10.0 mg of the compound obtained in Example 1, 60.0 mg of lactose and 35.0 mg of corn starch were mixed. This mixture was granulated through a sieve of 1 mm mesh, using 0.03 ml of a 10% aqueous solution of gelatin (containing 3.0 mg of gelatin), after which it was dried at 40° C. and again sieved. The resulting granules were mixed with 2.0 mg of magnesium stearate, followed by compression. The resulting core tablets were coated with a sugar coat, using an aqueous suspension of sucrose, titanium dioxide, talc and gum arabic. The coated tablets were polished with beeswax to yield finished coated tablets.

Preparation Example 2

| (1) Compound of Example 1 | 10.0 mg |
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound obtained in Example 1 and 3.0 mg of magnesium stearate were mixed. This mixture was granulated, using 0.07 ml of an aqueous solution of soluble starch (containing 7.0 mg of soluble starch), after which it was dried. The resulting granules were mixed with 70.0 mg of lactose and 50.0 mg of corn starch, followed by compression, to yield tablets.

Preparation Example 3

| (1) Compound of Example 1 | 5.0 mg |
| (2) Sodium chloride | 20.0 mg |
| (3) Distilled water was added to reach a total quantity of 2 ml. | |

5.0 mg of the compound obtained in Example 1 and 20.0 mg of sodium chloride were dissolved in distilled water, and diluted with water to reach a total quantity of 2.0 ml. The resulting solution was filtered and then aseptically packed in a 2 ml ampule. The ampule was sterilized and sealed to yield a solution for injection.

Experimental Example

Effect on platelet activating factor (PAF)-induced guinea pig bronchoconstriction Male Hartley guinea pigs (body weights about 500 g) were used. Bronchoconstriction induced by PAF, 1 µg/kg i.v., in guinea pigs was measured using to the method of Konzett-Roessler. With the guinea pig immobilized in the dorsal position, tracheotomy was performed under urethane (1.5 g/kg i.v.) anesthesia and the trachea was connected through a cannula to a respirator. The side branch of the tracheal cannula was connected to a transducer (model 7020, Ugobasile). With the volume of air per feed being controlled at 3–7 ml, the ventilation frequency at 70/min. and the pulmonary loading pressure at 10 cm $H_2O$, the volume of overflow air was recorded on a rectigraph (Recte-Hori-8s, San-ei Sokki) through the transducer. After administration of gallamine (1 mg/kg i.v.), PAF, 1 µg/kg, dissolved in physiological saline was administered through a jugular vein cannula and the induced bronchoconstriction was recorded for 15 minutes. The drug suspended in a 5% solution of gum arabic was administered orally in a dose of 10 mg/kg or 3 mg/kg one hour before PAF treatment: The results are presented in Table 1.

Table 1

Effect on PAF-induced bronchoconstriction in guinea pigs

| Example No. | % Inhibition of PAP-induced bronchoconstriction | |
|---|---|---|
| | 10 mg/kg | 3 mg/kg |
| 3 | 76 | — |
| 5 | 90 | — |
| 11 | 71 | 58 |
| 15 | — | 80 |
| 17 | — | 54 |
| 20 | — | 57 |

It will be apparent from Table 1 that the compound [I] or a salt thereof of the invention have excellent anti-PAF (platelet activity factor) activity.

What is claimed is:

1. A compound of the formula:

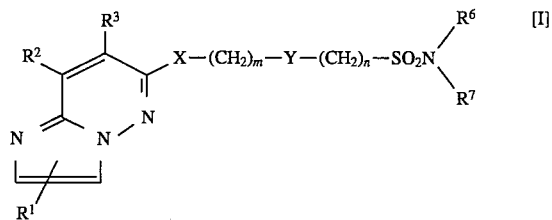

wherein $R^1$ stands for a hydrogen atom; $R^2$ and $R^3$ independently stand for a hydrogen atom or a $C_{1-3}$ alkyl group, provided that either $R^2$ or $R^3$ is a hydrogen atom, the other being a $C_{1-3}$ alkyl group; X stands for an oxygen atom; Y stands for a group of the formula:

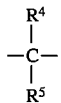

wherein $R^4$ and $R^5$ independently stand for a hydrogen atom or a $C_{1-3}$ alkyl group; $R^6$ and $R^7$ independently stand for a hydrogen atom or a $C_{1-3}$ alkyl group; m stands for 1; and n stands for 1 to 4, or a pharmaceutically acceptable salt thereof.

2. A compound as claimed in claim 1, wherein $R^2$ is a hydrogen atom and $R^3$ is a $C_{1-3}$ alkyl group.

3. 6-(2,2-dimethyl-3-sulfamoyl-1-propoxy) -7-methylimidazo [1,2-b]pyridazine.

4. 6-(2,2 -dimethyl -3- sulfamoyl -1-propoxy)-8 -methylimidazo [1,2,-b]pyridazine.

5. 6-(2,2 -diethyl -3- sulfamoyl -1-propoxy)-7 -methylimidazo [1,2-b]pyridazine.

6. An anti-asthmatic, anti-PAF, bronchoconstriction-inhibiting or anti-allergic composition which comprise an effective amount of a compound as claimed in claim 1 and a physiologically acceptable carrier.

7. An anti-asthmatic, anti-PAF, bronchoconstriction-inhibiting or anti-allergic composition which comprise an effective amount of a compound as claimed in claim 3 and a physiologically acceptable carrier.

8. An anti-asthmatic, anti-PAF, bronchoconstriction-inhibiting or anti-allergic composition which comprise an effective amount of a compound as claimed in claim 4 and a physiologically acceptable carrier.

9. An anti-asthmatic, anti-PAF, bronchoconstriction-inhibiting or anti-allergic composition which comprise an effective amount of a compound as claimed in claim 5 and a physiologically acceptable carrier.

10. A method for treating asthma in a mammal which comprises administering to a mammal suffering therefrom an effective amount of a compound as claimed in claim 1 with a physiologically acceptable carrier.

11. A method for treating asthma in a mammal which comprises administering to a mammal suffering therefrom an effective amount of a compound as claimed in claim 3 with a physiologically acceptable carrier.

12. A method for treating asthma in a mammal which comprises administering to a mammal suffering therefrom an effective amount of a compound as claimed in claim 4 with a physiologically acceptable carrier.

13. A method for treating asthma in a mammal which comprises administering to a mammal suffering therefrom an effective amount of a compound as claimed in claim 5 with a physiologically acceptable carrier.

14. A method for suppressing bronchismus or bronchoconstriction in a mammal which comprises administering to a mammal in need thereof an effective amount of a compound as claimed in claim 1 with a physiologically acceptable carrier.

15. A method for suppressing bronchismus or bronchoconstriction in a mammal which comprises administering to a mammal in need thereof an effective amount of a compound as claimed in claim 3 with a physiologically acceptable carrier.

16. A method for suppressing bronchismus or bronchoconstriction in a mammal which comprises administering to a mammal in need thereof an effective amount of a compound as claimed in claim 4 with a physiologically acceptable carrier.

17. A method for suppressing bronchismus or bronchoconstriction in a mammal which comprises administering to a mammal in need thereof an effective amount of a compound as claimed in claim 5 with a physiologically acceptable carrier.

* * * * *